(12) United States Patent
Yildirim

(10) Patent No.: US 10,937,542 B1
(45) Date of Patent: Mar. 2, 2021

(54) PATIENT SPECIFIC TREATMENT PLANNING

(71) Applicant: VENT CREATIVITY CORPORATION, Weehawken, NJ (US)

(72) Inventor: Gokce Yildirim, Weehawken, NJ (US)

(73) Assignee: VENT CREATIVITY CORPORATION, Weehawken, NJ (US)

(*) Notice: Subject to any disclaimer, the term of this patent is extended or adjusted under 35 U.S.C. 154(b) by 0 days.

(21) Appl. No.: 17/025,458

(22) Filed: Sep. 18, 2020

(51) Int. Cl.
*G16H 30/40* (2018.01)
*G16H 30/20* (2018.01)
*G06T 7/00* (2017.01)
*G06T 7/11* (2017.01)

(52) U.S. Cl.
CPC .......... *G16H 30/40* (2018.01); *G06T 7/0012* (2013.01); *G06T 7/11* (2017.01); *G16H 30/20* (2018.01); *G06T 2207/10028* (2013.01); *G06T 2207/20081* (2013.01); *G06T 2207/20084* (2013.01); *G06T 2207/20101* (2013.01)

(58) Field of Classification Search
CPC ...... G16H 30/20; G16H 30/40; G06T 7/0012; G06T 7/11; G06T 2207/10028; G06T 2207/20081; G06T 2207/20084; G06T 2207/20101

See application file for complete search history.

(56) References Cited

U.S. PATENT DOCUMENTS

| | | | |
|---|---|---|---|
| 9,452,050 | B2 | 9/2016 | Miles et al. |
| 10,292,770 | B2 | 5/2019 | Ryan et al. |
| 10,582,970 | B2 | 3/2020 | Yildirim et al. |
| 10,595,844 | B2 | 3/2020 | Nawana et al. |
| 2008/0221923 | A1 | 9/2008 | Shogan |
| 2010/0107270 | A1* | 4/2010 | Jones ............ A01H 5/10 800/263 |

(Continued)

FOREIGN PATENT DOCUMENTS

| EP | 1716535 A2 | 11/2006 |
|---|---|---|
| EP | 2754419 A2 | 7/2014 |

(Continued)

*Primary Examiner* — Nay A Maung
*Assistant Examiner* — Jose M Torres
(74) *Attorney, Agent, or Firm* — Dave Law Group LLC; Raj S. Dave

(57) ABSTRACT

A method of patient specific treatment planning is described herein. The method includes receiving an image file of a region of interest of an anatomy; extracting co-ordinates information and density information of a plurality of points of an image of the image file; pre-training a neural network based on the co-ordinates information, the density information and collective information of a database; performing at least one of a virtual action, and a treatment, via a user, on the region of interest based on collective information in the database; and training the neural network based on a user input, and the collective information from the database. The collective information comprises a plurality of clusters of different physiological states. The plurality of clusters comprises a plurality of sub-clusters. The virtual action and the treatment are performed through at least one of a virtual reality and an augmented reality.

20 Claims, 7 Drawing Sheets

(56) References Cited

U.S. PATENT DOCUMENTS

| | | | |
|---|---|---|---|
| 2010/0251117 A1* | 9/2010 | Baughman | G06N 3/006 |
| | | | 715/706 |
| 2014/0093153 A1 | 4/2014 | Sofka et al. | |
| 2015/0328004 A1 | 11/2015 | Mafhouz | |
| 2017/0148213 A1* | 5/2017 | Thomas | G06T 19/20 |
| 2018/0369611 A1* | 12/2018 | Owens | A61N 5/1049 |
| 2019/0005186 A1 | 1/2019 | Nikou et al. | |
| 2019/0183411 A1 | 6/2019 | Yildirim et al. | |
| 2019/0192880 A1* | 6/2019 | Hibbard | A61N 5/1039 |
| 2019/0333623 A1* | 10/2019 | Hibbard | G16H 20/40 |
| 2020/0170604 A1 | 6/2020 | Yildirim et al. | |
| 2020/0178885 A1* | 6/2020 | Orr | A61B 5/0205 |
| 2020/0205898 A1 | 7/2020 | Hampp et al. | |

FOREIGN PATENT DOCUMENTS

| | | |
|---|---|---|
| WO | 2020037308 A1 | 2/2020 |
| WO | 2020141812 A1 | 7/2020 |

* cited by examiner

PATIENT SPECIFIC TREATMENT PLANNING

FIELD OF THE INVENTION

This disclosure relates generally to patient specific treatment planning, and more particularly to segmentation, landmarking, labeling, pre-treatment, and post-treatment recovery tracking.

BACKGROUND

"Systems and methods for generating a surgical plan for altering an abnormal bone using a generic normal bone model are discussed. For example, a system for planning a surgery on an abnormal bone can include a model receiver module configured to receive a generic normal bone model. The generic normal bone model, such as a parametric model derived from statistical shape data, can include a data set representing a normal bone having an anatomical origin comparable to the abnormal bone. An input interface can be configured to receive an abnormal bone representation including a data set representing the abnormal bone. A surgical planning module can include a registration module configured to register the generic normal bone model to the abnormal bone representation by creating a registered generic model. A surgical plan formation module can be configured to identify one or more abnormal regions of the abnormal bone using the registered generic model." [Source: Systems and methods for using generic anatomy models in surgical planning; Constantinos Nikou, Branislav Jaramaz; published as US20190005186A1 on 3 Jan. 2019].

"Methods and devices are disclosed relating improved articular models, implant components, and related guide tools and procedures. In addition, methods and devices are disclosed relating articular models, implant components, and/or related guide tools and procedures that include one or more features derived from patient-data, for example, images of the patient's joint. The data can be used to create a model for analyzing a patient's joint and to devise and evaluate a course of corrective action. The data also can be used to create patient-adapted implant components and related tools and procedures." [Source: Patient-adapted and improved orthopedic implants, designs and related tools; Raymond A. Bojarski, Nam Chao, John Slamin, Thomas Minas, Philipp Lang, Wolfgang Fitz, Daniel Steines, Terrance Wong; published as EP2754419A2 on 16 Jul. 2014].

"[t]he automatic bone segmentation may also include automatic segmentation of metal structures in the target joint area. In an advantageous implementation, metal structures are automatically segmented in the medical image data using intensity thresholding. Metal appears very bright in CT images and can therefore be accurately differentiated from bone structures and other tissue by extracting voxels having an intensity above a certain threshold." [Source: Method and System for Bone Segmentation and Landmark Detection for Joint Replacement Surgery; Michal Sofka, Meizhu Liu, Dijia Wu, Shaohua Kevin Zhou; published as US20140093153A1 on 3 Apr. 2014].

"Various systems and methods are provided for surgical and interventional planning, support, post-operative follow-up, and functional recovery tracking. In general, a patient can be tracked throughout medical treatment including through initial onset of symptoms, diagnosis, non-surgical treatment, surgical treatment, and recovery from the surgical treatment. In one embodiment, a patient and one or more medical professionals involved with treating the patient can electronically access a comprehensive treatment planning, support, and review system. The system can provide recommendations regarding diagnosis, non-surgical treatment, surgical treatment, and recovery from the surgical treatment based on data gathered from the patient and the medical professional(s). The system can manage the tracking of multiple patients, thereby allowing for data comparison between similar aspects of medical treatments and for learning over time through continual data gathering, analysis, and assimilation to decision-making algorithms." [Source: Systems and methods for surgical and interventional planning, support, post-operative follow-up, and functional recovery tracking; Namal Nawana, William C. Horton, William J. Frasier, Cody Cranson, Max Reinhardt, Mark T. Hall, Matthew Parsons, Jennifer DiPietro, Kevin Lee, Michelle LaWare, John P. Griffin, Sean P. Selover, Jonathan Bellas, Douglas Raymond, Nicholas Pavento, Mary L. Fowler, Dennis Chien; published as U.S. Ser. No. 10/595,844B2 on 24 Mar. 2020].

FIG. 1 illustrates a traditional process of segmentation that recognizes a segment of a region of interest of an image as a bone based on a single predefined threshold value, according to a prior art. The traditional process of segmentation, described herein, assigns the single predefined threshold value to the region of interest. The traditional process of segmentation analyses the segment of the region of interest and when a Hounsfield unit of the segment of the region of interest is above the single predefined threshold value, then the segment of the region of interest is recognized and/or categorized as the bone. However, the traditional process of segmentation is not able to separate and depict two fused bones of different density values (as depicted in 102) as the region of interest is assigned with the single predefined threshold value, and as resolution of the image is low. At 102, the two bones of different density values are fused and shown together, where a user is not able to readily identify and analyze different segments (e.g. bones) present in the region of interest. Therefore, there is a long felt need to identify, locate, and depict bones of different density values.

Considering the knowledge of persons skilled in the art, there is a long-felt need for patient specific treatment planning based on density, multi-thresholding and kinematics associated with the region of interest.

SUMMARY OF INVENTION

Disclosed are one or more aspects of patient specific treatment planning.

In one aspect, a method is described herein. The method comprises receiving an image file of a region of interest of an anatomy; extracting co-ordinates information and density information of a plurality of points of the image file; pre-training a neural network based on the co-ordinates information, the density information and collective information available in a database; performing at least one of a virtual action and a treatment, via a user, on the region of interest based on an input from the neural network to generate an output for the user; and training the neural network based on at least one of a user input from the user and the collective information from the database. The anatomy comprises a bodily structure of a living organism. The collective information comprises a plurality of clusters of different physiological states of the living organism.

In an embodiment, the method comprises recording the co-ordinates information and the density information of the region of interest on the database; recording first information, on the database, based on the virtual action and the treatment on the region of interest under a first cluster of the plurality of clusters of different physiological states to which the region of interest belongs; and recording second information on the database, under the first cluster of the plurality of clusters of different physiological states to which the region of interest belongs, based on at least one of outcome of the treatment, and a feedback from the user.

In another embodiment, recording the second information on the database comprises updating the first information on the database based on at least one of the outcome of the treatment, and the feedback from the user.

In yet another embodiment, extracting the co-ordinates information and the density information of the plurality of points comprises creating point cloud information of the anatomy based on the co-ordinates information, the density information, and the collective information.

In yet another embodiment, creating the point cloud information of the anatomy comprises generating a heat map of the anatomy based on the point cloud information, the heap map indicates a location of a first bone, a second bone and a foreign object within the region of interest.

In yet another embodiment, generating the heat map indicating the location of the first bone, the second bone and the foreign object comprises automatically assigning a first threshold value to the first bone, a second threshold value to the second bone and a third threshold value to the foreign object based on the density information In yet another embodiment, performing the virtual action comprises performing at least one of segmenting a segment of the region of interest; landmarking the segment of the region of interest; labeling the segment of the region of interest; and creating a treatment plan for the region of interest.

In yet another embodiment, performing the virtual action further comprises; recommending at least one of a treatment procedure, the treatment plan, and a treatment location of the region of interest based on the collective information in the database.

In yet another embodiment, segmenting the segment of the region of interest comprises generating a heat map based on point cloud information of the anatomy; assigning a threshold value to the segment of the region of interest; estimating Hounsfield units of the plurality of points of the image file; outlining the segment of the region of interest; and determining at least one of an edge and a tunnel on the region of interest based on the Hounsfield units.

In yet another embodiment, determining at least one of the edge and the tunnel on the region of interest comprises: determining density value of the plurality of points of the region of interest; and determining a plurality of first points on the region of interest as at least one of the edge and the tunnel, when the plurality of first points comprises a first density value lower than a second density value of a plurality of second points. The plurality of second points located on either side of the plurality of first points.

In yet another embodiment, landmarking the segment of the region of interest comprises identifying a ligament attachment point and a tendon attachment point on the region of interest and creating planes and lines on the region of interest.

In yet another embodiment, landmarking the segment of the region of interest comprises: identifying a first cluster from the plurality of clusters of different physiological states to which the region of interest belongs; correlating a virtual kinematic model of the region of interest with a predefined virtual kinematic model of the first cluster; analyzing motion of the virtual kinematic model and predicting a constraint and a constraint location for the virtual kinematic model; determining a first position and a first angle for at least one of a ligament attachment point and a tendon attachment point in the virtual kinematic model at a first level; and determining a second position and a second angle for at least one of the ligament attachment point and the tendon attachment point in the virtual kinematic model at a second level, when the first position and first angle fails to create an optimum kinematics in the virtual kinematic model.

In yet another embodiment, landmarking the segment of the region of interest comprises categorizing information associated with the region of interest under a sub-cluster of the cluster based on at least one of the ligament attachment point and the tendon attachment point.

In yet another embodiment, the collective information comprises at least one of pre-stored information, the co-ordinates information and the density information of the region of interest, first information recorded based on the virtual action and the treatment on the region of interest, and second information recorded based on at least one of outcome of the treatment and a feedback from the user.

In yet another embodiment, recording the first information on the database comprises recording remarks information indicating at least one of a first outcome and a second outcome of the treatment.

In yet another embodiment, recording the remarks information comprises recording a plurality of first parameters and a plurality of second parameters that contribute to the first outcome and the second outcome, respectively.

In yet another embodiment, the plurality of clusters of different physiological states comprises a first cluster, and a second cluster.

In yet another embodiment, the plurality of clusters of different physiological states comprises at least one of a third cluster based on landmarks of the region of interest, a fourth cluster based on a tendon attachment point, and a fifth cluster based on a ligament attachment point of the region of interest.

In yet another embodiment, the pre-stored information comprises third information with respect to a first cluster, a second cluster, a third cluster, a fourth cluster and a fifth cluster.

In yet another embodiment, the pre-stored information comprises at least one of a predefined virtual kinematic model; a predefined treatment location; a predefined treatment procedure; a predefined treatment plan; and predefined density information.

In yet another embodiment, creating the treatment plan for the region of interest comprises: analyzing a defect on the region of interest; simulating a virtual kinematic model of the region of interest; identifying a first cluster from the plurality of clusters of different physiological states to which the region of interest belongs; correlating the virtual kinematic model with a predefined virtual kinematic model of the first cluster; analyzing motion of the predefined virtual kinematic model and predicting a constraint and a constraint location for the virtual kinematic model; and creating at least one of a treatment procedure, the treatment plan, a tendon attachment point, and a ligament attachment point for the region of interest.

In yet another embodiment, identifying the first cluster from the plurality of clusters of different physiological states to which the region of interest belongs comprises: recording information associated with the region of interest under a new cluster when the region of interest does not belong to the first cluster, the new cluster comprises a sub-cluster.

In yet another embodiment, creating the treatment plan comprises: recovering kinematics and retaining an activity of daily living (ADL) of the living organism.

In yet another embodiment, retaining the activity of daily living comprises: retaining the activity of daily living by recovering the kinematics of the region of interest back to the first cluster; and retaining the activity of daily living by recovering the kinematics of the region of interest back to a second cluster.

In yet another embodiment, retaining the activity of daily living comprises: retaining the activity of daily living by performing a regression analysis based on the collective information in the database.

In yet another embodiment, labeling the segment of the region of interest comprises: labeling the segment of the region of interest based on the density information and the co-ordinates information.

In yet another embodiment, the plurality of clusters of different physiological states comprises a plurality of sub-clusters.

In yet another embodiment, the collective information comprises the plurality of clusters of different physiological states with respect to age, gender, race, geographic location, and morphology.

In yet another embodiment, assigning the threshold value to the segment of the region of interest comprises: identifying a first segment and a second segment of the region of interest based on the co-ordinates information and the density information; and assigning a first threshold value and a second threshold value to the first segment and the second segment of the region of interest, respectively.

In yet another embodiment, the living organism comprises an animal, a bird, a mammal, and a human being.

In yet another embodiment, the user comprises at least one of a surgeon, a physician, a care taker, a medical practitioner, and a machine.

In yet another embodiment, the machine comprises at least one of an automated machine and a semi-automated machine.

In yet another embodiment, receiving the image file of the region of interest of the anatomy comprises receiving the image file of the region of interest as a Digital Imaging and Communications in Medicine (DICOM) format file.

In yet another embodiment, retaining the activity of daily living by recovering the kinematics of the region of interest back to one of the first cluster and the second cluster comprises: recovering the kinematics with a compensation factor and estimating a return score to one of the first cluster and the second cluster.

In yet another embodiment, the method comprises: communicating wirelessly the collective information, and one of a processed image output and a processed video output of the virtual action to a device associated with the user.

In yet another embodiment, performing at least one of the virtual action, and the treatment, via the user, on the region of interest comprises: performing at least one of the virtual action, and the treatment on the region of interest through at least one of a virtual reality and an augmented reality.

In yet another embodiment, performing the virtual action further comprises: generating at least one of a three-dimensional (3D) virtual kinematic model of the region of interest and a processed image file of the region of interest based on the co-ordinates information, the density information, and the collective information of the database; simulating the three-dimensional (3D) virtual kinematic model to virtually display functioning of the region of interest to the user; and assisting the user to perform the treatment on the region of interest.

In yet another embodiment, generating at least one of the three-dimensional (3D) virtual kinematic model of the region of interest and the processed image file of the region of interest comprises depicting a treatment procedure on the region of interest.

In yet another embodiment, depicting the treatment procedure on the region of interest comprises at least one of displaying a boundary on the region of interest, indicating a virtual cut on the region of interest, and indicating a position of screws on the region of interest.

In yet another embodiment, displaying the boundary on the region of interest guides the user not to perform an intervention within the boundary during the treatment.

In yet another embodiment, generating at least one of the three-dimensional (3D) virtual kinematic model and the processed image file of the region of interest comprises indicating a first feature in a first color and a first identifier and a second feature in a second color and a second identifier respectively.

In yet another embodiment, generating at least one of the three-dimensional (3D) virtual kinematic model of the region of interest and the processed image file of the region of interest comprises enabling at least one of an automated machine and a semi-automated machine to print a three-dimensional (3D) physical incarnation of at least one of the processed image file and the three-dimensional (3D) virtual kinematic model of the region of interest.

In yet another embodiment, generating at least one of the three-dimensional (3D) virtual kinematic model of the region of interest and the processed image file of the region of interest comprises enabling at least one of an automated machine and a semi-automated machine to provide a virtual reality version and an augmented reality version of the three-dimensional (3D) virtual kinematic model and the processed image file.

In yet another embodiment, providing the virtual reality version and the augmented reality version of the three-dimensional (3D) virtual kinematic model and the processed image file comprises enabling the user to perform the treatment on the region of interest through one of remotely and directly.

In yet another embodiment, printing the three-dimensional physical incarnation of at least one of the processed image file and the three-dimensional (3D) virtual kinematic model of the region of interest comprises indicating a first feature of the three-dimensional physical incarnation with a first color and a first identifier and a second feature of the three-dimensional physical incarnation with a second color and a second identifier.

In yet another embodiment, indicating the first feature of the three-dimensional physical incarnation with the first color and the first identifier and the second feature of the three-dimensional physical incarnation with the second color and the second identifier comprises enabling at least one of the automated machine and the semi-automated machine to track the three-dimensional physical incarnation and recognize colors and identifiers on the three-dimensional physical incarnation.

In yet another embodiment, enabling at least one of the automated machine and the semi-automated machine to track the three-dimensional physical incarnation and recognize the colors and the identifiers on the three-dimensional physical incarnation comprises enabling at least one of the automated machine and the semi-automated machine to mimic a tool held by the user and perform the treatment remotely as directed by the user.

In yet another embodiment, enabling at least one of the automated machine and the semi-automated machine to track the three-dimensional physical incarnation and recognize the colors and the identifiers on the three-dimensional physical incarnation comprises enabling at least one of the automated machine and the semi-automated machine to track a location of a first bone and depict at least one of a potential implant position, a screw position and a plate position for optimum fixation.

In yet another embodiment, enabling at least one of the automated machine and the semi-automated machine to print the three-dimensional physical incarnation of at least one of the processed image file and the three-dimensional (3D) virtual kinematic model of the region of interest comprises: positioning the three-dimensional physical incarnation and performing one of a two-dimensional (2D) spot-check and diagnosis X-rays; and checking one of a pre-op X-ray, a post-op X-ray and 2D image.

In yet another embodiment, generating at least one of the three-dimensional (3D) virtual kinematic model of the region of interest and the processed image file of the region of interest comprises: enabling the user to virtually turn-on and turn-off individual layers of the segment.

In another aspect, a system is described. The system comprises a server comprising a memory, and a processor communicatively coupled to the memory. The processor configured to receive an image file of a region of interest of an anatomy; extract co-ordinates information and density information of a plurality of points of an image of the image file; pre-train a neural network based on the co-ordinates information, the density information and collective information available in a database; perform at least one of a virtual action and a treatment, via a user, on the region of interest based on an input from the neural network to generate an output for the user; and train the neural network based on at least a user input from the user, and the collective information from the database. The anatomy comprises a bodily structure of a living organism. The collective information comprises a plurality of clusters of different physiological states of the living organism.

In yet another aspect, non-transitory computer storage medium storing a sequence of instructions is described herein. The sequence of instructions which when executed by a processor, causes: receiving an image file of a region of interest of an anatomy; extracting co-ordinates information and density information of a plurality of points of the image file; pre-training a neural network based on the co-ordinates information, the density information and collective information available in a database; performing at least one of a virtual action and a treatment, via a user, on the region of interest based on an input from the neural network to generate an output for the user; and training the neural network based on at least one of a user input from the user and the collective information from the database.

In yet another aspect, a database is described herein. The database comprises collective information comprising pre-stored information, co-ordinates information and density information of a region of interest, first information collected based on a virtual action and a treatment on the region of interest, and second information collected based on an outcome of the treatment and a feedback from a user. The collective information comprises a plurality of clusters of different physiological states of a living organism.

In an embodiment, the second information comprises the first information that are updated based on at least one of the outcome of the treatment, and the feedback from the user.

In another embodiment, the first information on the database comprises remarks information indicating at least one of a first outcome and a second outcome of the treatment.

In yet another embodiment, the remarks information comprises a plurality of first parameters and a plurality of second parameters that contributes to the first outcome and the second outcome of the treatment, respectively.

In yet another embodiment, the plurality of first parameters comprises at least one of a treatment procedure, a treatment plan, and a treatment location that contributes to the first outcome.

In yet another embodiment, the plurality of second parameters comprises at least one of a treatment procedure, a treatment plan, and a treatment location that contributes to the second outcome.

In yet another embodiment, the collective information comprises at least one of a processed image output and a processed video output of at least one of a virtual action and a treatment on the region of interest.

The methods and systems disclosed herein may be implemented in any means for achieving various aspects and may be executed in a form of a non-transitory machine-readable medium embodying a set of instructions that, when executed by a machine, causes the machine to perform any of the operations disclosed herein. Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Figure 1:
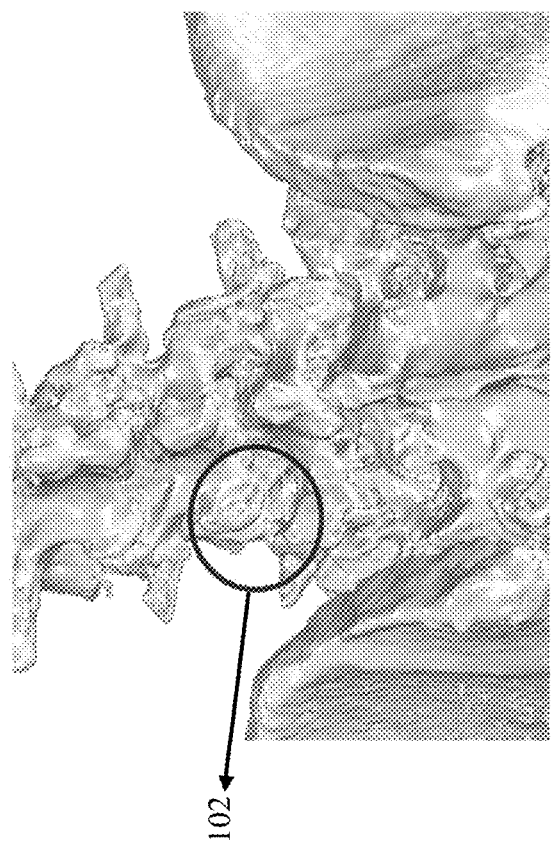
FIG. 1 illustrates a traditional process of segmentation that recognizes a segment of a region of interest of an image as a bone based on a single predefined threshold value, according to a prior art.

Other features of the present embodiments will be apparent from the accompanying drawings and from the detailed description that follows.

DETAILED DESCRIPTION

The articles "a" and "an" are used herein refers to one or to more than one (i.e., to at least one) of the grammatical object of the article. By way of example, "an element" means one element or more than one element.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

Implementations may be realized in a computing system that includes a back end component, e.g., as a data server, or that includes a middleware component, e.g., an application server, or that includes a front end component, e.g., a client computer having a graphical user interface or a Web browser through which a user may interact with an implementation, or any appropriate combination of one or more such back end, middleware, or front end components. The components of the system may be interconnected by any appropriate form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

Embodiments of the present invention may comprise or utilize a special purpose or general-purpose computer including computer hardware. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described. Rather, the described features and acts are disclosed as example forms of implementing the claims.

Processors suitable for the execution of a computer program include, by way of example, both general and special purpose microprocessors, and any one or more processors of any appropriate kind of digital computer. Generally, a processor will receive instructions and data from a read only memory or a random-access memory or both. Elements of a computer can include a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer may be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in, special purpose logic circuitry.

To provide for interaction with a user, implementations may be realized on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any appropriate form of sensory feedback, e.g., visual feedback, auditory feedback, or tactile feedback; and input from the user may be received in any appropriate form, including acoustic, speech, or tactile input.

In order to fully understand the scope of the invention, the following terms used herein are hereby defined.

The term "comprising", which is synonymous with "including", "containing", or "characterized by" here is defined as being inclusive or open-ended, and does not exclude additional, unrecited elements or method steps, unless the context clearly requires otherwise.

The term "device" is defined as an electronic element that cannot be divided without destroying its stated function.

The term "user" as used herein refers to a surgeon, a medical practitioner, a physician, a care taker, a doctor, an automated machine, and a semi-automated machine.

The term "server" is defined as a computer that manages network resources.

The term "communicatively coupled" is defined as devices connected in a way that permits communication.

The term "configured" is defined as arranged within the system to perform certain functions.

The term "receiving" is defined as being given information.

The term "region of interest" as used herein refers to a subset of an image adapted for a particular purpose.

The term "image" as used herein refers to a representation of an internal and/or external form of a living organism.

The term "image file" as used herein refers to a file that comprises graphics data.

The term "cluster" as used herein refers to a group of physiological states of the living organism.

The term "sub cluster" as used herein refers to a subset of the cluster.

The term "living organism" as used herein refers to an organism that shows characteristics of being alive.

The term "anatomy" as used herein refers to structure and internal workings of the living organism.

The term "collective information" as used herein refers to whole information available in a database at that instant.

The term "outcome" as used herein refers to a consequence or result of a treatment performed on the region of interest.

The term "based on" is defined as dependent on.

The term "a plurality of" is defined as multiple.

The term "memory" is defined as any device in which information can be stored.

The term "execute" is defined as run or launch.

The term "instructions" is defined as software program or machine executable code.

The term "neural network" as used herein refers to a computational learning system that uses a network of functions to understand and translate a data input of one form into a desired output, usually in another form.

The term "pretraining" as used herein refers to a training provided to a neural network prior to started doing a particular task.

The term "virtual action" as used herein refers to an action that is performed within a virtual environment.

The term "treatment" as used herein refers to a medical care given to the living organism. The treatment also refers to a use of an agent, procedure, or a regimen, such as a drug or surgery, or exercise, in an attempt to cure or mitigate a disease, condition, injury or illness.

The term "physiological state" as used herein refers to a condition or state of a body or a bodily function of the living organism. The physiological state may be one among a plurality of healthy cluster states or one among a plurality of unhealthy cluster states.

The term "point cloud" as used herein refers to a collection of data points defined by a given co-ordinates system. The point cloud is as bunch of points that are connected to each other.

The term "co-ordinates" as used herein refers to a set of values that show an exact position.

The term "outlining" as used herein refers to marking a boundary of the region of interest.

The term "component" is intended to be broadly construed as hardware, firmware, and/or a combination of hardware and software.

The term "foreign object" as used herein refers to an object/thing that is present in a body but does not belong to the body.

The term "threshold" as used herein refers to a limit that must be exceeded for a certain reaction, phenomenon, result, or condition to occur.

The term "labeling" as used herein refers to describing someone or something in a word or short phase.

The term "segmenting" as used herein refers to a division of the region of interest into segments.

The term "landmarks" as used herein refers to locations on a bone that is accepted to be a reproducible feature, and also ligament attachments and tendon attachments that are relevant for kinematics.

The term "processor" is defined as a component in the server for executing instructions stored in memory.

The term "transceivers" is defined as a component used for both transmission and reception of digital data.

The term "pre-stored information" as used herein refers to the information that is stored in an advance in a database of being needed to do a particular task.

The term "ADL" as used herein refers to activity of daily living i.e. a task of everyday life.

The term "kinematics" as used herein refers to aspects of motion of the body of the living organism.

The term "incarnation" as used herein refers to a physical form of the region of interest. The incarnation is made up of any metal and/or any material.

Example embodiments, as described below, may be used to provide patient specific treatment planning. It will be appreciated that the various embodiments discussed herein need not necessarily belong to the same group of embodiments and may be grouped into various other embodiments not explicitly disclosed herein. In the following description, for purposes of explanation, numerous specific details are set forth in order to provide a thorough understanding of the various embodiments.

Implementations and all of the functional operations described in this specification may be realized in digital electronic circuitry, or in computer software, firmware, or hardware.

A software program (also known as a program, software, executable code or instructions) may be written in any appropriate form of programming language, including compiled or interpreted languages, and it may be deployed in any appropriate form, including as a standalone program or as a module, component, subroutine, or other unit suitable for use in a computing environment.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described should not be understood as requiring such separation in all implementations, and it should be understood that the described program components and systems may generally be integrated together in a single software product or packaged into multiple software products.

Even though particular combinations of features are recited in the claims and/or disclosed in the specification, these combinations are not intended to limit the disclosure of possible implementations. Other implementations are within the scope of the following claims. For example, the actions recited in the claims may be performed in a different order and still achieve desirable results. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

In an aspect, the present disclosure discloses patient specific treatment planning. An image file of a region of interest of an anatomy is received. The anatomy comprises a bodily structure of a living organism. The image file may comprise a video file. Co-ordinates information and density information of a plurality of points of an image of the image file are extracted. A neural network is pretrained based on the co-ordinates information, the density information and collective information available in a database. A virtual action and/or a treatment on the region of interest is performed, via a user, based on the collective information on the database. The neural network is further trained based on at least one of a user input, and the collective information from the database. The patient specific treatment planning finds application in at least one of but not limited to a sports medicine, a trauma, an orthopedics, etc.

Figure 2:
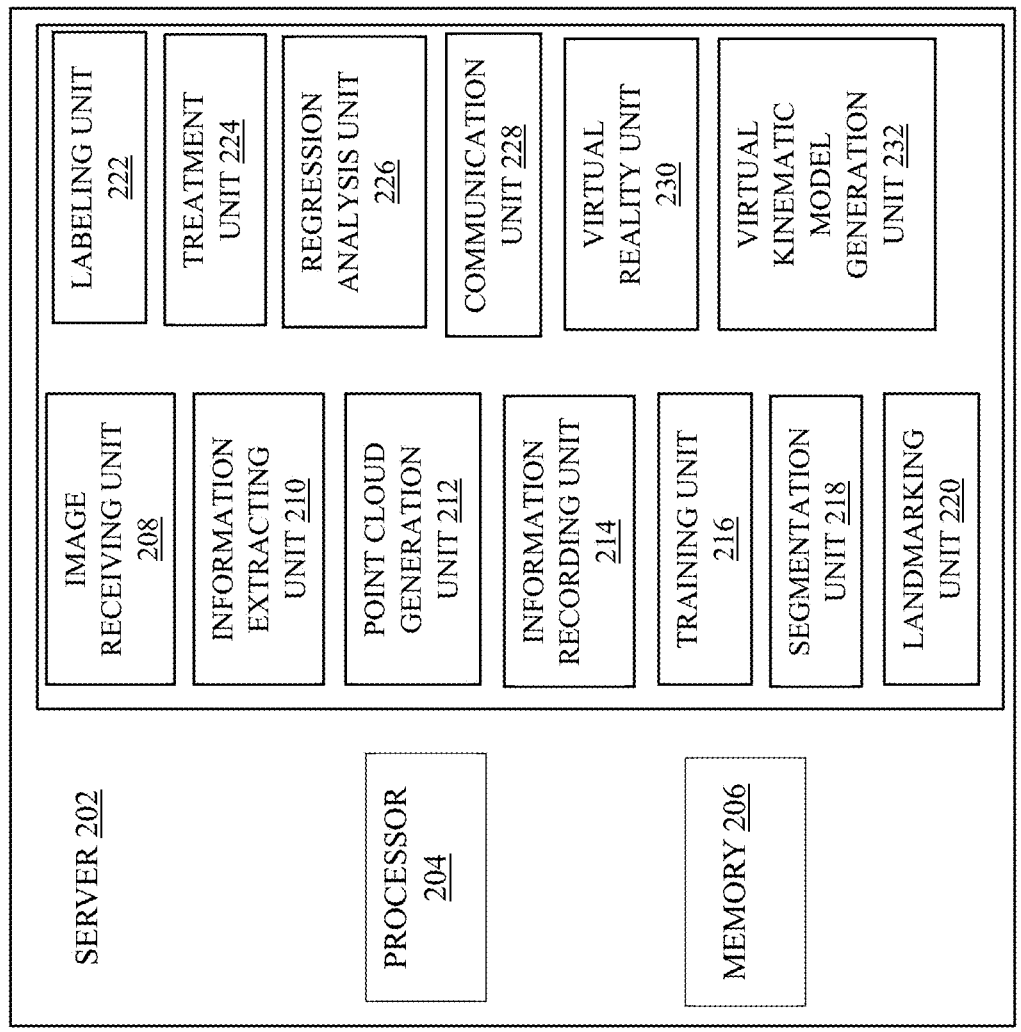
FIG. 2 illustrates an exploded view of a server, according to one or more embodiments.

FIG. 2 illustrates an exploded view of a server 202, according to one or more embodiments. The server 202 disclosed herein comprises a memory 206 and a processor 204. The processor 204 is communicatively coupled to the memory 206. The processor 204 may take a form of a single core processor, multi-core processor (e.g., a dual core processor, triple core processor, quad core processor, etc.), microprocessor, etc. In some embodiments, the processor 204 may be external to an apparatus (e.g. server), for example the processor 204 may be a remote processor (e.g., a cloud-based processor). Alternatively, or additionally, the processor 204 may be internal and/or local to the apparatus. The server 202 further comprises an image receiving unit 208, an information extracting unit 210, a point cloud generation unit 212, an information recording unit 214, a training unit 216, a segmentation unit 218, a landmarking unit 220, a labeling unit 222, a treatment unit 224, a regression analysis unit 226, a communication unit 228, a virtual reality unit 230 and a virtual kinematic model generation unit 232. The above-mentioned units in association with the processor is configured to perform patient specific treatment planning. The image receiving unit 208 receives an image file and/or a video file of a region of interest of an anatomy. The anatomy comprises a bodily structure of a living organism. The region of interest may be any part and/or any portion (e.g. a skull, a shoulder, a spine, a knee, a foot, etc.) of the living organism. The anatomy belongs to the living organism. In an embodiment the living organism comprises one of an animal, a human being, a bird, and a mammal. The image file comprises an image and/or a video of the region of interest. The image file comprises one of a Digital Imaging and Communications in Medicine (DICOM) format file, a computed tomography (CT) image file and a magnetic resonance imaging (MRI) format file. In an embodiment, the image file may comprise the video file.

The image receiving unit 208 receives the image file from an image source. The image comprises a plurality of points (e.g. a plurality of pixels, a plurality of voxels, etc.). The image comprises one of a two-dimensional image and a three-dimensional image. In an embodiment, size of the plurality of points comprises one of three by three millimeter cubes and one by one millimeter cubes. In another embodiment, the size of the plurality of points of the image file ranges from 3*3*3 mm cubes to 0.6*0.6*0.6 mm cubes that represents voxels of information and/or pixels of information. In an embodiment, the voxels of information and/or the pixels of information comprise density information. The information extracting unit 210 extracts co-ordinates information and the density information of each point of the plurality of points of the image. The point cloud generation unit 212 generates point cloud information of the region of interest of the anatomy based on the co-ordinates information and the density information. In an embodiment, the point cloud generation unit 212 generates a heat map of the region of interest based on the point cloud information. The heat map distinguishes between a segment of the region of interest with different colors.

The information recording unit 214 records the co-ordinates information and the density information on a database under a plurality of clusters of different physiological states. The database comprises pre-stored information. The pre-stored information comprises a predefined virtual kinematic model, a predefined treatment location, a predefined treatment procedure, a predefined treatment plan, gait data, force data, and predefined density information with respect to each cluster of the plurality of clusters of different physiological states. The plurality of clusters of different physiological states comprises a first cluster (e.g. a healthy cluster state), a second cluster (e.g. an unhealthy cluster state), a third cluster (e.g. an existing cluster state), etc. The plurality of clusters of different physiological states further comprises a fourth cluster based on landmarks of the region of interest, a fifth cluster based on a tendon attachment point and a sixth cluster based on a ligament attachment point of the region of interest.

The training unit 216 pretrains a neural network based on the co-ordinates information, the density information, and collective information of the database. In an embodiment, the neural network is a convolutional neural network. The segmentation unit 218 segments (e.g. divides, splits) the segment of the region of interest. The segment may comprise a first segment (e.g. a first bone), a second segment (e.g. a second bone), a third segment (e.g. a foreign object), etc. In an embodiment, the first bone comprises a dense bone, the second bone comprises a soft bone and the foreign object comprises a metal object. In another embodiment, the first bone comprises a first bone section comprising a first gradient density, a second bone section comprising a second gradient density, etc. The training unit 216 pretrains the neural network to readily distinguish and locate the first bone section, the second bone section, etc. within the first bone, based on the first gradient density, the second gradient density, etc., respectively. The segmentation unit 218 estimates Hounsfield units of the segment of the region of interest. The segmentation unit 218 further assigns a first threshold value, a second threshold value and a third threshold value to the first segment, the second segment and the third segment, respectively. For example, the first threshold value ranges from 0 to 20% for the first segment (e.g. cancellous bone), the second threshold value ranges from 20% to 80% for the second segment (e.g. cortical bone) and the third threshold value ranges over 2000 Hounsfield units for the third segment (e.g. the foreign object). In an embodiment, percentage values vary for the first segment, the second segment, and the third segment varies and joint types of the first segment, the second segment, and the third segment of each patient of different populations.

The segmentation unit 218 further outlines the first segment, the second segment and the third segment based on the Hounsfield units and marks boundaries associated with the first segment, the second segment and the third segment. For an instance, when the Hounsfield units estimated from the image file ranges from −1024 to 3000 or more, the threshold value is 2500 Hounsfield units or higher for the third segment (e.g. the foreign object) and the highest percentage value assigned is 100%. The Hounsfield units −1024 range corresponds to air. In an embodiment, the training unit 216 trains the neural network with different threshold values for the third segment (e.g. the foreign objects) made of different metals to automatically identify and locate the first segment, the second segment and the third segment. The segmentation unit 218 further determines at least one of an edge and a tunnel between and/or within the segment of the region of interest and determines whether the segment is one segment or two segments. The segmentation unit 218 determines a first density value of a plurality of first points and a second density value of a plurality of second points of the plurality of points in the image file. The plurality of second points are located on either side of the plurality of first points. The segmentation unit 218 determines the plurality of first points as the edge and/or the tunnel, when the plurality of first points comprising the first density value lower than the second density value of the plurality of second points. In an embodiment, the first density value of the plurality of first points is lower than one of 0% to 20% and 20% to 80% of the second density value of the plurality of second points. In another embodiment, the segmentation unit 218 segments sub-segments within the segment. For an example, the segmentation unit 218 segments the region of interest and detects whether the region of interest comprises one bone or two bones within the segment of the region of interest.

The landmarking unit 220 landmarks the segment of the region of interest based on kinematics associated with the segment of the region of interest. The landmarking unit 220 identifies the first cluster (e.g. the healthy cluster state) of the plurality of clusters of different physiological states to which the region of interest belongs. In an embodiment, the cluster (e.g. the first cluster) to which the region of interest belongs is identified using k-nearest neighbor (KNN) analysis. The landmarking unit 220 correlates a virtual kinematic model of the region of interest with the predefined virtual kinematic model of the first cluster. In an embodiment, the first cluster (e.g. the healthy cluster state) comprises multiple clusters based on at least one of the landmarks, the ligament attachment point, the tendon attachment point, and the virtual kinematic models with respect to activity of daily livings (ADLs). The landmarking unit 220 analyzes the kinematics (e.g. motion) associated with the virtual kinematic model and predicts a constraint and a constraint location for the virtual kinematic model. The landmarking unit 220 further determines a first position and a first angle for at least one of the ligament attachment point and the tendon attachment point in the virtual kinematic model at a first level to create/restore an optimum kinematics in the virtual kinematic model. The landmarking unit 220 further determines a second position and a second angle for at least one of the ligament attachment point and the tendon attachment point in the virtual kinematic model at a second level to create/restore the optimum kinematics in the virtual kinematic model, when the first position and the first angle fails to create/restore the optimum kinematics.

The labeling unit 222 labels the segment of the region of interest once the segment of the region is landmarked and segmented. The labeling unit 222 labels the segment of the region of interest from one of left to right, right to left, top to bottom and bottom to top. For a first instance, the labeling unit 222 labels the segment of the region of interest from top to bottom, in which a skull is labelled as Z and a foot is labelled as −Z. For a second instance, the labeling unit 222 labels a left knee as +X and a right knee as −X. In an embodiment, the labelling unit 222 enables the user to readily identify and distinguish between the segments of the region of interest. In another embodiment, the labelling unit 222 enables to verify accuracy of the labeling performed on the region of interest and correct the labelling when the accuracy is below a predefined accuracy.

The treatment unit 224 creates a treatment plan for the region of interest. The treatment unit 224 analyzes a defect on the region of interest. The treatment unit 224 simulates the virtual kinematic model of the region of interest and identifies the first cluster from the plurality of clusters of different physiological states to which the region of interest belongs. The treatment unit 224 correlates the virtual kinematic model with the predefined virtual kinematic model of the first cluster. The treatment unit 224 analyzes the kinematics (e.g. motion) associated with the virtual kinematic model of the region of interest and predicts the constraint and the constraint location for the region for the virtual kinematic model to restore the optimum kinematics in the virtual kinematic model of the region of interest. In an embodiment, the treatment unit 224 restores the optimum kinematics by creating virtual points to position/place flexions, extension, attachments, etc. on the region of interest. The treatment unit 224 creates the treatment plan that optimizes the kinematics, a treatment location, etc. The treatment unit 224 then creates the treatment plan relevant to a cluster (e.g. the first cluster, the second cluster, the third cluster, etc.) of the plurality of clusters of different physiological states to which the region of interest belongs. In an embodiment, the treatment unit 224 then creates the treatment plan to the region of interest based on the kinematics, force data, gait data, etc. associated with the healthy cluster state relevant to the region of interest available in the database at that instant. In an embodiment, the treatment unit 224 creates a first set of rules for the first cluster to which the region of interest belongs. In another embodiment, the first set of rules can be imposed on the region of interest to recover the region of interest. In another embodiment, the treatment unit 224 creates the set of rules for each cluster of the plurality of clusters of different physiological states. In another embodiment, the treatment unit 224 enables the user to register and perform a treatment on the region of interest. The treatment plan comprises a treatment type, a treatment procedure, the ligament attachment point, and the tendon attachment point of the region of interest. In an embodiment, the treatment unit 224 creates the treatment plan to recover the kinematics and retain an activity of daily living of the living organism. The activity of daily living comprise sitting, standing, walking, running, etc. In another embodiment, the treatment unit 224 recovers the kinematics with a compensation factor and estimates a return score to one of the first cluster, the second cluster, the third cluster, etc. In yet another embodiment, the treatment unit 224 retains the activity of daily living back to one of the first cluster (e.g. the healthy cluster state), the second cluster (e.g. the unhealthy cluster state), the third cluster (e.g. the existing cluster state), etc. In yet another embodiment, the treatment unit 224 enables the user to interact with the region of interest on the fly (i.e. during the treatment) and plan the treatment (e.g. orienting an implant at an optimal position, an optimal angle, etc.).

The regression analysis unit 226 performs a regression analysis to perform a cluster correction (i.e. converting the region of interest from one cluster to another cluster). In an embodiment, the regression analysis unit 226 finds the first cluster (e.g. the healthy cluster state) equivalent to the region of interest to analyze the kinematics associated with the healthy cluster state and impose the kinematics on the region of interest. In another embodiment, the regression analysis unit 226 determines at least one parameter from the region of interest that are intended to identify that the region of interest belongs to the first cluster of the plurality of clusters of different physiological states. The information recording unit 214 records first information and second information on the database, in addition to the pre-stored information under the plurality of clusters of different physiological states. The information recording unit 214 records the first information based on a virtual action and the treatment performed on the region of interest. The first information comprises remarks information indicating an outcome of the treatment. The outcome of the treatment comprises a first outcome (e.g. good outcome), a second outcome (e.g. bad outcome), etc. The remarks information further comprises a plurality of first parameters and a plurality of second parameters that contributes to the first outcome and the second outcome, respectively. The plurality of first parameters may comprise first physics assumptions and the plurality of second parameters may comprise second physics assumptions. The information recording unit 214 records the second information based on at least one of the outcome of the treatment and a feedback received from a user. In an embodiment, the user comprises at least one of a surgeon, a physician, a care taker, a medical practitioner, and a machine. The machine comprises at least one of a semi-automated machine, and an automated machine.

The information recording unit 214 updates the first information on the database based on at least one of the outcome of the treatment and the feedback received from the user. The first information updated comprises a plurality of third parameters and a plurality of fourth parameters that contributes to the first outcome and the second outcome, respectively. In an embodiment, the plurality of third parameters comprises parameters less than or equal to the plurality of first parameters and the plurality of fourth parameters comprises parameters less than or equal to the plurality of second parameters. The virtual action comprises at least one of segmentation, landmarking, labeling, and creating a treatment plan on the region of interest. The virtual action further comprises recommending the treatment plan for the region of interest. The database comprises the collective information. The collective information comprises the pre-stored information, the first information and the second information. The training unit 216 then trains the neural network based on at least one of a user input and the collective information on the database. The user input is received while performing the virtual action and the treatment on the region of interest. In an embodiment, the training unit 216 trains the neural network to a threshold point and/or limit and records the collective information on the database where the sever 202 can function independently without getting an input from the neural network to provide an output to the user.

The information recording unit 214 categorizes and records the collective information under the plurality of clusters of different physiological states. In an embodiment, the information recording unit 214 categorizes and records information associated with the region of interest under a new cluster when the region of interest does not belong to the plurality of clusters of different physiological states. In another embodiment, the information recording unit 214 records the information associated with the region of interest under the plurality of clusters of different physiological states based on at least one of the ligament attachment point, the tendon attachment point and the landmarks of the region of interest. The plurality of clusters of different physiological states further comprises the fourth cluster (e.g. a cluster based on the landmarks of the region of interest), the fifth cluster (e.g. a cluster based on the tendon attachment point), the sixth cluster (e.g. a cluster based on the ligament attachment point), etc. In yet another embodiment, the information recording unit 214 records the information associated with the region of interest under a plurality of sub-clusters of the plurality of clusters of different physiological states.

The communication unit 228 communicates the collective information, and one of a processed image output and a processed video output to a device associated with the server. In an embodiment, the communication unit 228 communicates wirelessly the collective information, and one of the processed image output and the processed video output to the device associated with the server 202. In another embodiment, the communication unit 228 communicates the collective information, and one of the processed image output and the processed video output to the device associated with the server 202, through a wired network. The virtual reality unit 230 provides the processed image output and the processed video output in least one of a virtual reality and an augmented reality enables the user to perform the virtual action and the treatment on the region of interest through at least one of the virtual reality and the augmented reality.

The virtual kinematic model generation unit 232 generates at least one of the virtual kinematic model and a processed image file of the region of interest based on one of the co-ordinates information, the density information, and the collective information of the database. The virtual kinematic model comprises a three-dimensional virtual kinematic model. The virtual kinematic model generation unit 232 simulates the virtual kinematic model. The virtual kinematic model generation unit 232 virtually displays the functioning of the region of interest and assists the user to perform the treatment on the region of interest. In an embodiment, the virtual kinematic model generation unit 232 assists the user to perform the treatment by depicting the treatment plan (e.g. the treatment procedure) on the region of interest.

The treatment procedure depicted on the region of interest comprises at least one of displaying a boundary on the region of interest, indicating a virtual cut on the region of interest, indicating a position of screws on the region of interest, etc. The virtual kinematic model generation unit 232 displays the boundary on the region of interest and guides the user not to perform an intervention within the boundary during the region of interest. The virtual kinematic model generation unit 232 further indicates a first feature (e.g. the first segment), a second feature (e.g. the second segment), a third feature (e.g. the foreign object) etc. in the virtual kinematic model with the first color and the first identifier, the second color and the second identifier, and the third color and the third identifier etc. respectively. In an embodiment, the virtual kinematic model generation unit 232 further indicates the first feature (e.g. the first segment), the second feature (e.g. the second segment), the third feature (e.g. the foreign object) etc. in the virtual kinematic model with the first color and the first identifier, the second color and the second identifier, and the third color and the third identifier etc. respectively to track a location of a dense bone and depict at least one of a potential implant position, a screw position and a plate position with respect to optimum fixation.

The virtual kinematic model generation unit 232 further enables the machine to print a three-dimensional (3D) physical incarnation of at least one of the processed image file and the virtual kinematic model of the region of interest. The three-dimensional (3D) physical incarnation comprises a physical prototype of the region of interest (e.g. bones). The physical prototype of the region of interest enables the user to view and analyze functioning (e.g. the kinematics) of the three-dimensional physical incarnation. In an embodiment, the virtual kinematic model generation unit 232 further enables the machine to print the three-dimensional (3D) physical incarnation comprising the first feature, the second feature and the third feature with the first color and the first identifier, the second color and the second identifier, and the third color and the third identifier, respectively. In another embodiment, the virtual kinematic model generation unit 232 further positions the three-dimensional physical incarnation, performs one of a two-dimensional (2D) spot-check and diagnosis X-rays to check orientation in surgery, and to check one of a pre-op X-ray, a post-op X-ray and 2D image for extracting three-dimensional physical incarnation information. In yet another embodiment, the virtual kinematic model generation unit 232 further enables the machine to track the three-dimensional (3D) physical incarnation and recognize the first color and the first identifier, the second color and the second identifier, and the third color and the third identifier, etc. In yet another embodiment, the virtual kinematic model generation unit 232 further enables the machine to mimic a tool held by the user and perform the treatment remotely as directed by the user. In yet another embodiment, the virtual kinematic model generation unit 232 enables the user to turn-on and turn-off individual layers of the segment to identify location of different categories of body parts, make decisions and create the treatment plan.

Figure 3:
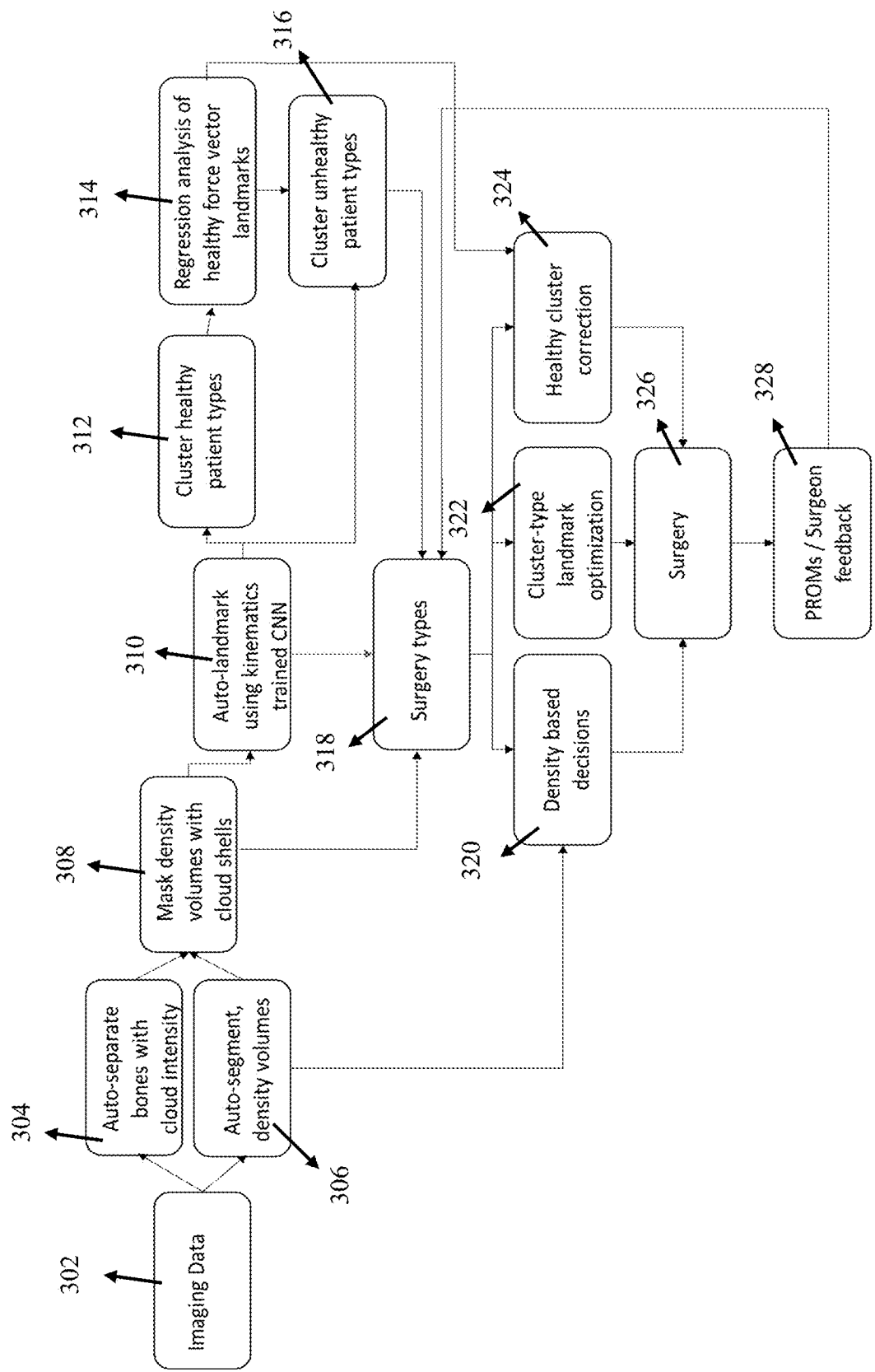
FIG. 3 illustrates a method of patient specific treatment planning, according to one or more embodiments.

FIG. 3 illustrates a method of patient specific treatment planning, according to one or more embodiments. At step 302, an image file of a region of interest of an anatomy is received. The image file comprises an image and/or a video. The image file may comprise a video file. The image and/or the video may be a medical image and/or a medical video of the region of interest. In an embodiment, the image comprises a plurality of points. In an embodiment, the plurality of points comprises one of a plurality of pixels and a plurality of voxels. The anatomy may belong to a living organism. The anatomy comprises a bodily structure of the living organism. In an embodiment, the living organism comprises an animal, a bird, a mammal, and a human being. The image file comprises one of a Digital Imaging and Communications in Medicine (DICOM) format file, a computed tomography (CT) image file and a magnetic resonance imaging (MRI) format file. The image comprises resolution of points depending on size of the plurality of points. In an embodiment, the size of the plurality of points ranges from 0.6*0.6*0.6 mm cubes to 3*3*3 mm cubes that represents one of voxels of information and pixels of information from the computed tomography (CT) image file and the magnetic resonance imaging (MRI) format file. The plurality of points comprises density information. Once the image file is received, the density information and co-ordinates information of each point of the plurality of points in the image is extracted. The density information and the co-ordinates information are recorded on a database. Based on the density information, the co-ordinates information and collective information of the database, a neural network is pretrained. The database comprises pre-stored information. In an embodiment, the pre-stored information comprises at least one of a predefined virtual kinematic model, a predefined treatment location, a predefined treatment procedure, a predefined treatment plan, and predefined density information.

In an embodiment, point cloud information of the anatomy is created based on the density information, the co-ordinates information, and the pre-stored information. In another embodiment, a heat map of the anatomy is generated based on the point cloud information. The heat map indicates a segment and a foreign object (e.g. an object). The segment comprises a first segment (e.g. a dense bone), a second segment (e.g. a soft bone), etc. In an embodiment, the foreign object comprises a metal object.

Once the neural network is pretrained, an auto separation (i.e. a virtual action) of the segment is performed, at step 304, based on the collective information in the database. In an embodiment, the auto separation is performed based on the density information (e.g. intensity). The auto separation comprises assigning a threshold value to the segment of the region of interest. The assignment of the threshold value to the region of interest comprises assigning a first threshold value to the first segment, a second threshold value to the second segment, and a third threshold value to the foreign object. In an embodiment, the first segment, the second segment and the foreign object are identified and located on the region of interest based on the density information and the co-ordinates information. Based on the first threshold value, the second threshold value and the third threshold value, the auto separation is performed. The auto separation comprises an edge detection. The edge detection comprises estimation of Hounsfield units in addition to the assignment of the threshold value. The estimation of Hounsfield units comprises detecting and estimating the Hounsfield units of each point of the plurality of points in the image. Based on the estimated Hounsfield units of each point of the plurality of points in the image, the segment of the region of interest is outlined automatically. In an embodiment, the first segment of the region of interest is outlined with a first color and a first identifier, the second segment of the region of interest is outlined with a second color and a second identifier. In another embodiment, the segment of the region of interest is outlined either by manually, automatically or by semi-automatically.

An auto segmentation (i.e. the virtual action) is performed based on the density information at step 306. The auto segmentation comprises detection of at least one of an edge and a tunnel in the region of interest. The detection of at least one of the edge and the tunnel in the region of interest comprises determining a plurality of first points of the plurality of points as at least one of the edge and the tunnel, when the plurality of first points comprises a first density value lower than a second density value of a plurality of second points. The plurality of second points is located on either side of the plurality of first points. In an embodiment, the plurality of first points comprises the first density value lower than one of 0% to 20% and 20% to 80% of the second density value of the plurality of second points.

In an embodiment, the neural network is trained to enable the server 202 to categorize and/or record the collective information under a first cluster (e.g. the healthy cluster state) comprising various sub-clusters (e.g. the physiological states) of a second cluster (e.g. the unhealthy cluster state). In another embodiment, the neural network is trained to enable the server 202 to categorize and/or record the collective information under the second cluster (e.g. the unhealthy cluster state) comprising various sub-clusters (e.g. the physiological states) of the first cluster (e.g. the healthy cluster state). In yet another embodiment, the neural network is trained to make decision on the segmentation and masking of the segment of the region of interest based on the collective information available in the database without any need to execute the virtual action for individual segment of the region of interest each time. In another embodiment, the neural network is trained to learn from the collective information available in the database and execute at least one of the virtual action, and the treatment on boundaries of the segment of the region of interest obtained using validated approaches.

At step 308, the plurality of first points (e.g. the edge, the tunnel, etc.) are masked with a processed image output of the virtual action and the plurality of first points are deleted to have only desired segments of the region of interest. The desired segments can be achieved on the region of interest by performing Boolean addition and/or Boolean subtraction. At step 310, an auto landmarking (i.e. the virtual action) is performed to landmark the segment of the region of interest using the neural network. The landmarking comprises identifying at least one of a ligament attachment point and a tendon attachment point on the region of interest. The ligament attachment point and the tendon attachment point may be identified to create planes and lines on the region of interest and determine couplings (e.g. mechanical axis cut versus anatomical axis cut) that are adapted to perform the treatment and recover kinematics on the region of interest.

In an embodiment, the neural network is trained using predefined kinematics of the anatomy. The kinematics associated with the region of interest is analyzed and correlated with the predefined kinematics of a plurality of clusters of different physiological states in the database to identify one of the first cluster, the second cluster, etc. of the plurality of clusters of different physiological states to which the region of interest belongs. In an embodiment, the kinematics associated with the region of interest is analyzed and correlated with the predefined kinematics of the plurality of clusters of different physiological states with respect to age and an activity of daily living (ADL). At step 312, the region of interest is categorized under the first cluster of the plurality of clusters of different physiological states upon identifying that the region of interest belongs to the first cluster. In an embodiment the first cluster comprises a healthy cluster state. At step 314, a regression analysis is performed to categorize the region of interest under the second cluster, upon identifying that the region of interest does not belong to the first cluster. In an embodiment, the regression analysis is performed to determine at least one parameter from the region of interest that are intended to identify a cluster from the plurality of clusters of different physiological states to which the region of interest belongs. In another embodiment, the regression analysis is further performed to determine minimum number of parameters among total number of parameters from the region of interest that are intended to identify the cluster from the plurality of clusters of different physiological states to which the region of interest belongs. At step 316, the region of interest is categorized under the second cluster of the plurality of clusters of different physiological states upon identifying that the region of interest belongs to the second cluster. In an embodiment the second cluster comprises an unhealthy cluster state. In another embodiment, the region of interest is categorized under a new cluster when the region of interest does not belong to one of the first cluster, the second cluster, a third cluster, etc. In yet another embodiment, the plurality of clusters of different physiological states comprises a fourth cluster based on the landmarks of the region of interest, a fifth cluster based on the tendon attachment point and a sixth cluster based on the ligament attachment point of the region of interest.

The auto landmarking further comprises simulating a virtual kinematic model of the region of interest and correlating the virtual kinematic model with the predefined virtual kinematic model of one of the first cluster, the second cluster, etc. to which the region of interest belongs. Once the correlation is performed, motion associated with virtual kinematic model of the region of interest is analyzed and a constraint and a constraint location for the virtual kinematic model is predicted. A first position and a first angle for at least one of the ligament attachment point and the tendon attachment point in the virtual kinematic model is determined at a first level to create/restore the kinematics in the virtual kinematic model. A second position and a second angle for at least one of the ligament attachment point and the tendon attachment point in the virtual kinematic model is then determined at a second level, when the first position and first angle fails to create/restore the kinematics in the virtual kinematic model. Based on the ligament attachment point and the tendon attachment point in the virtual kinematic model of the region of interest, the region of interest is categorized under a sub-cluster of at least one of the first cluster, the second cluster, etc. Further, based on the density information and the co-ordinates information the segment of the region of interest is labelled. In an embodiment, the labeling is performed to train the neural network. In an embodiment, the labeling is performed to enable the user to readily distinguish between the segment of the region of interest.

At step 318, a treatment type is created based on at least one of the auto landmarking and the cluster of which the region of interest belongs. In an embodiment, the treatment type is recommended/selected based on the cluster of the plurality of clusters of different physiological states to which the region of interest belongs. The treatment type comprises a treatment procedure, a treatment location and a treatment plan of the region of interest. In an embodiment, creating the treatment type comprises recovering the kinematics and retaining the activity of daily living (ADL) to one of the first cluster (e.g. a healthy cluster state), the second cluster (e.g. an unhealthy cluster state), the third cluster (e.g. an existing cluster state). In another embodiment, the kinematics is recovered with a compensation factor and estimating a return score to one of the healthy cluster state and the existing cluster state. In another embodiment, creating the treatment type comprises calculation of implant type used for a joint of the region of interest to prevent impingement of one of a physical device (e.g. a tool held by the user during the treatment) and a component of the physical device on a patient's body during the treatment.

Upon creating the treatment type, density-based decisions are performed at step 320. The density-based decisions comprise identifying a position, an angle and a cut that are to be performed on the region of interest to perform the treatment (e.g. an orthopedic implant) on the region of interest. At step 322, a landmark optimization is performed with respect to the cluster (to which the region of interest belongs) is based on the treatment type created. The landmark optimization varies depending on the treatment type. At step 324, a cluster correction is performed based on the regression analysis.

Once the virtual action (i.e. the auto separation, the auto segmentation, the auto landmarking, the labeling, and creating the treatment plan) is performed, first information is recorded based on the virtual actual and the treatment performed on the region of interest. The first information comprises the treatment type (i.e. the treatment procedure, the treatment location, and the treatment plan) performed on the region of interest. The first information comprises remarks information of the treatment type that is performed on the region of interest. The remarks information indicates an outcome of the treatment. The outcome of the treatment comprises a first outcome (e.g. good outcome) and a second outcome (e.g. bad outcome). The remarks information further comprises a plurality of first parameters and a plurality of second parameters that contribute to the first outcome and the second outcome of the treatment, respectively. A processed image output and a processed video output, obtained as a result of the virtual action, is communicated to a user.

In an embodiment, a virtual kinematic model of the region of interest and a processed image file of the region of interest is generated and simulated based on the co-ordinates information, the density information, and the collective information of the database. The virtual kinematic model of the region of interest comprises a three-dimensional virtual kinematic model. The three-dimensional (3D) virtual kinematic model and the processed image file of the region of interest is then communicated to a device associated with the user. The three-dimensional (3D) virtual kinematic model and the processed image file comprises the treatment procedure depicted on the region of interest. The treatment procedure comprises at least one of displaying a boundary on the region of interest, indicating a virtual cut on the region of interest, indicating a position of screws on the region of interest, etc. In an embodiment, the boundary is displayed to assist and alert the user not to perform an intervention within the boundary during the treatment.

In another embodiment, the three-dimensional (3D) virtual kinematic model and the processed image file comprises a first feature and a second feature indicated in a first color and a first indicator, and a second color and a second indicator, respectively. In yet another embodiment, the three-dimensional (3D) virtual kinematic model and the processed image file comprising the first feature and the second feature is adapted to print a three-dimensional (3D) physical incarnation of at least one of the processed image file and the three-dimensional (3D) virtual kinematic model of the region of interest. In yet another embodiment, the three-dimensional (3D) virtual kinematic model and the processed image file comprising the first feature and the second feature is adapted to track a three-dimensional (3D) physical incarnation of at least one of the processed image file and the three-dimensional (3D) virtual kinematic model of the region of interest.

In yet another embodiment, the processed image file and the three-dimensional (3D) virtual kinematic model of the region of interest is generated to provide a virtual reality version and an augmented reality version of the three-dimensional (3D) virtual kinematic model and the processed image file. In yet another embodiment, the virtual reality version and the augmented reality version of the three-dimensional (3D) virtual kinematic model and the processed image file is adapted to enable the user to perform the treatment on the region of interest either remotely or directly. In yet another embodiment, tracking the three-dimensional (3D) physical incarnation comprises indicating the first feature with the first color and the first identifier, and the second feature with the second color and the second identifier, etc. In yet another embodiment, tracking the three-dimensional (3D) physical incarnation of at least one of the processed image file and the three-dimensional (3D) virtual kinematic model of the region of interest is adapted to mimic the tool held by the user and perform the treatment remotely as directed by the user. In yet another embodiment, tracking the three-dimensional (3D) physical incarnation of at least one of the processed image file and the three-dimensional (3D) virtual kinematic model of the region of interest is adapted to track a location of the first segment (e.g. the dense bone) and depict at least one of a potential implant position, a screw position, a plate position for optimum fixation, etc. In yet another embodiment, printing the three-dimensional physical incarnation is adapted to position the three-dimensional physical incarnation and perform one of a two-dimensional (2D) spot-check and diagnosis X-rays to check orientation in surgery; and check one of a pre-op X-ray, a post-op X-ray and 2D image for extracting three-dimensional physical incarnation information. The three-dimensional (3D) virtual kinematic model and the processed image file of the region of interest is further adapted to virtually turn-on and turn-off individual layers of the segment to identify location of different categories of body parts, make decisions and create the treatment plan. In an embodiment, the virtual kinematic model is overlaid on one of the three-dimensional (3D) physical incarnation and a physical bone of a patient. In another embodiment, the virtual kinematic model overlaid on one of the three-dimensional (3D) physical incarnation and the physical bone of the patient is seen and interacted (e.g. the treatment) with using a virtual reality environment and an augmented reality environment.

At step 326, the treatment is performed on the region of interest via the user based on at least one of the density-based decisions, the landmark optimization, and the cluster correction. In an embodiment, the user comprises at least one of a surgeon, a physician, a care taker, a medical practitioner, and a machine. The machine comprises at least one of an automated machine and a semi-automated machine. In an embodiment, the virtual action and the treatment on the region of interest is performed through one of the virtual reality environment and the augmented reality environment.

Once the treatment is performed, a feedback from the user (e.g. the surgeon) and a patient reported outcome measures (PROM) is received, at step 328. The feedback from the surgeon comprises confirmation from the surgeon that the region of interest belongs to the cluster (e.g. the first cluster, the second cluster, etc.) of the plurality of clusters of different physiological states, etc. The PROM is received from a patient to whom the treatment is performed. Based on the feedback from the user and the patient reported outcome measures (PROM), the second information is recorded on the database. Further, based on at least one of the feedback from the user and the patient reported outcome measures (PROM), the first information is updated on the database. The updating of the first information on the database comprises updating at least one of the treatment type, the plurality of first parameters, the plurality of second parameters, the plurality of third parameters, the plurality of fourth parameters, the remarks information, the plurality of clusters of different physiological states, the first physics assumptions, the second physics assumptions, etc.

Based on the first information updated on the database, the information is looped back to the database, and the neural network is getting trained. As the first information in the database is getting updated and updated, the neural network is capable of suggesting the treatment type suitable to the region of interest by verifying a minimum (e.g. ten parameters) number of parameters instead of looking all the parameters (e.g. hundred parameters) that contributes to one of the first outcome and the second outcome. The collective information on the database is categorized under the plurality of clusters of different physiological states with respect to age, gender, race, geographic location, morphology, etc.

Figure 4:
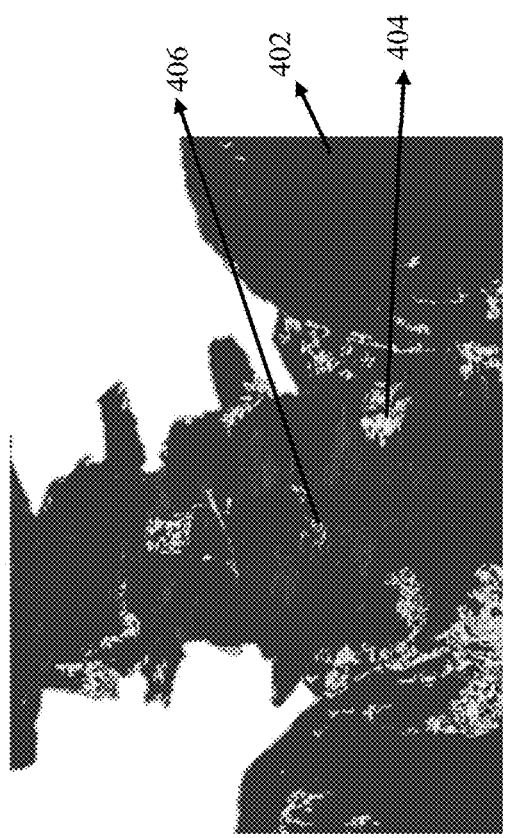
FIG. 4 illustrates a first processed image output of an auto segmentation of a segment of a region of interest, according to one or embodiments.

FIG. 4 illustrates a first processed image output of the auto segmentation of the segment of the region of interest, according to one or embodiments. The region of interest comprises the first segment 402, the second segment 404, the third segment 406 etc. The first segment 402, the second segment 404 and the third segment 406 comprise the first density value, the second density value and a third density value, respectively. The Hounsfield unit detection is performed on the region of interest to identify and locate the first segment 402, the second segment 404 and the third segment 406 (e.g. the foreign object, the tunnel, the edge, etc.). The auto segmentation, described herein, assigns the first threshold value to the first segment 402 (e.g. the dense bone), the second threshold value to the second segment 404 (e.g. the soft bone) and the third threshold value to the third segment 406 (e.g. the foreign object). In an embodiment, the first threshold value, the second threshold value and the third threshold value are assigned based on the Hounsfield unit detection on the region of interest. Since the first segment 402, the second segment 404 and the third segment 406 are assigned with the first threshold value, the second threshold value and the third threshold value, respectively, the server 202 automatically segments and displays the first segment 402 the second segment 404, the third segment 406, etc. of the region of interest. The first segment 402, the second segment 404, the third segment 406, etc. is outlined and indicated with different colors and different identifiers to enable the user to readily distinguish and identify the first segment 402, the second segment 404, the third segment 406, etc.

The Hounsfield unit detection is further performed to determine at least one of the edge and the tunnel on the region of interest. The density value of the plurality of points on the image file of the region of interest is determined. The plurality of first points of the plurality of points is determined as at least one of the edge and the tunnel on the region of interest when the plurality of first points comprising the first density value is lower than the second density value of the plurality of second points. The plurality of second points are located on the either side of the plurality of first points. In an embodiment, the plurality of first points comprises the first density value lower than one of 0% to 20% and 20% to 80% of the second density value of the plurality of second points.

Figure 5:
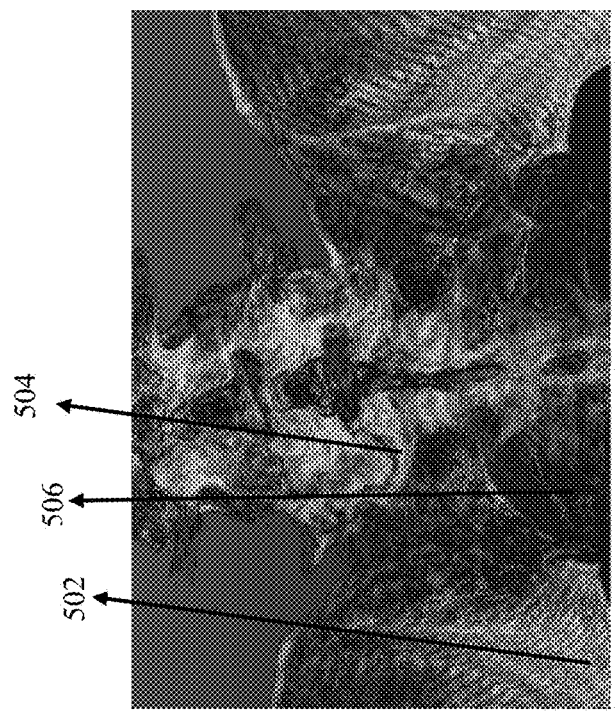
FIG. 5 illustrates a second processed image output of point cloud information of a region of interest, according to one or more embodiments.

FIG. 5 illustrates a second processed image output of the point cloud information of the region of interest, according to one or more embodiments. The image file of the region of interest is received by the server 202. The image file comprises the image. The density information and the co-ordinates information of the plurality of points of the image is extracted. The density information and the co-ordinates information are used to create the point cloud information of the region of interest. The point cloud information comprises the bunch of points. The point cloud information is not a solid surface object. The point cloud information further does not comprise connections between the bunch of points. The point cloud information allows to mask the plurality of second points around the plurality of first points in the point cloud and delete the plurality of second points. In an embodiment, the plurality of second points are deleted automatically. In another embodiment, the plurality of second points are deleted semi-automatically. In yet another embodiment, the plurality of second points are deleted manually. In yet another embodiment, the edge and/or the tunnel 506 is identified among the bunch of points of the point cloud information between the first segment 502 (e.g. the first bone), the second segment 504 (e.g. the second bone), etc. of the region of interest. The first segment 502, the second segment 504, the edge and/or the tunnel 506 is indicated with different colors and different identifiers to enable the user to readily identify and distinguish the first bone, the second bone and the edge.

The user is then allowed, by the server 202, to mask the plurality of second points of the first bone and the second bone and delete the plurality of first points of the edge and/or the tunnel. Once the edge and/or the tunnel 506 is deleted from the region of interest, the first segment 502 (e.g. the first bone) and the second segment 504 (e.g. the second bone) on the region of interest is left on the point cloud information. In an embodiment, the region of interest is labelled by at least one of automatically, semi-automatically and manually. In another embodiment, the region of interest is labelled from one of top to bottom, bottom to top, left to right and right to left. For a first instance, in case of labelling the region of interest from the top to bottom, then a skull is a labelled as Z and a foot is labelled as −Z. For a second instance, in case of labelling a left knee and right knee, the left knee is labelled as +X and right knee is labelled as −X. For a third instance, when the treatment plan for the left knee is created automatically, the treatment plan (e.g. angled cut, etc.) for the right knee is mirrored and created automatically. Similarly, when the treatment plan is created for a left hand, the treatment plan for a right hand is mirrored and created automatically.

Figure 6:
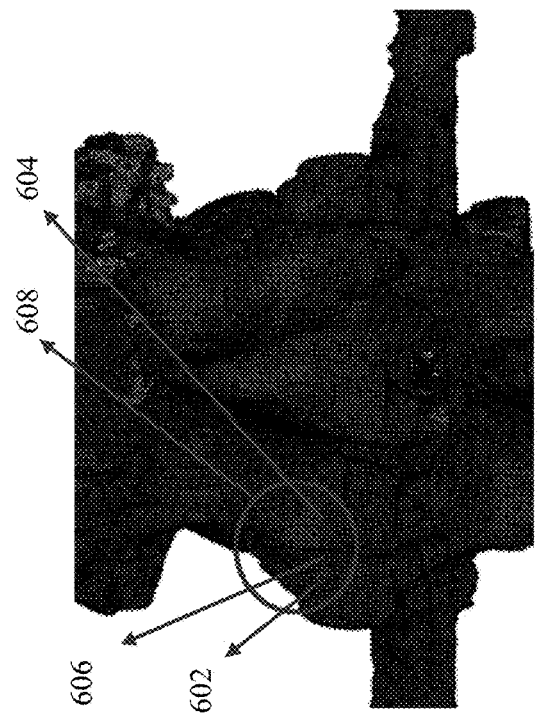
FIG. 6 illustrates a third processed image output of a virtual action, according to one or more embodiments.

FIG. 6 illustrates a third processed image output of the virtual action, according to one or more embodiments. The point cloud information is generated from the image file received. The point cloud information comprises the bunch of points that are not connected with each other. The point cloud information comprises shells and encapsulates the first segment, the second segment, the third segment, etc. Masks (i.e. the shells) on the point cloud information are taken and enforced on top of the first processed image output of the auto segmentation (e.g. FIG. 4) to get the third processed image. The third processed image output depicts the first segment with the first color and the first identifier (e.g. a first label), the second segment with the second color and the second identifier (e.g. a second label), and the third segment with the third color and the third identifier (e.g. a third label). The first segment, the second segment and the third segment comprising the first density value, the second density value and the third density value respectively is readily identified based on the first color and the first identifier (e.g. a first label), the second segment with the second color and the second identifier (e.g. a second label), and the third segment with the third color and the third identifier (e.g. a third label) respectively. At 608, the third processed image output clearly depicts the edge/the tunnel 606 between the first segment 602 and the second segment 604 of the region of interest.

For a first instance, in an orthopedic implantation, based on the location of the first segment (e.g. the dense bone), the user is allowed to figure out where to place trajectories and find entry points of screws. In an embodiment, based on the location of the first segment (e.g. the dense bone), the user is allowed to place the screw and create a sphere around a sphere of influence (e.g. four or five millimeters). The plurality of points that touch the sphere are determined as entry points and the trajectories are created and from the plurality of points, the neural network determines whether the landmarks are on the region of interest. In an embodiment, once the first cluster (e.g. the dense bone) relevant to the region of interest is identified, the trajectories for the entry points and exit points of the screw are generated and a factorial of all possible combinations of the entry points and the exit points is generated. In an embodiment, the trajectories and the factorial of all possible combinations of the entry points and the exit points are filtered based on at least one predefined rule. The predefined rule is set with respect to at least one of a thread engagement to the first segment (e.g. the dense bone), diameter of the screw contacting the first segment (e.g. the dense bone), length of the screw engaging a volume of the dense bone, etc. In an embodiment, the trajectories and the factorial of all possible combinations of the entry points and the exit points are filtered and reduced to a smaller subset based on neural network driven solutions to recommend/provide the treatment plan to the user. A plurality of lines of the dense bone along its path are determined based on parameters of at least one of a pitch of the screw, a diameter of the screw and the length of the screw. Based on the parameters, the user is able to recognize and identify a type of screw to use, a thread of the screw and the trajectory for optimum fixation.

For a second instance, in an unicondylar knee arthroplasty, the exact location of the dense bone in the third processed image output enables the user to identify the dense bone among the region of interest and to make a predefined cut (e.g. a halfmoon shape cut) on exactly the dense bone (e.g. tibia), instead of inadvertently making the predefined cut on the soft bone. Inadvertently creating the predefined cut on the soft bone impacts a micro motion or a larger motion on the region of interest.

For a third instance, the third processed image output enables the user to identify readily a primary implant (e.g. the foreign object) from the region of interest. The third processed image output further enables the user to discover readily the first segment (e.g. the dense bone) in which the primary implant is fixed earlier, and screw type attachments for revision surgery once the primary implant is removed. In an embodiment, removing the primary implant from the region of interest may comprise removing stock of the dense bone from the region of interest as the primary implant has fixed to the first segment (e.g. the dense bone) and the first segment remaining on the region of interest is difficult to determine with imaging techniques. The third processed image output depicts the first segment remaining on the region of interest even after removing the primary implant and the stock of the dense bone and enables to register and perform the revision surgery.

Figure 7:
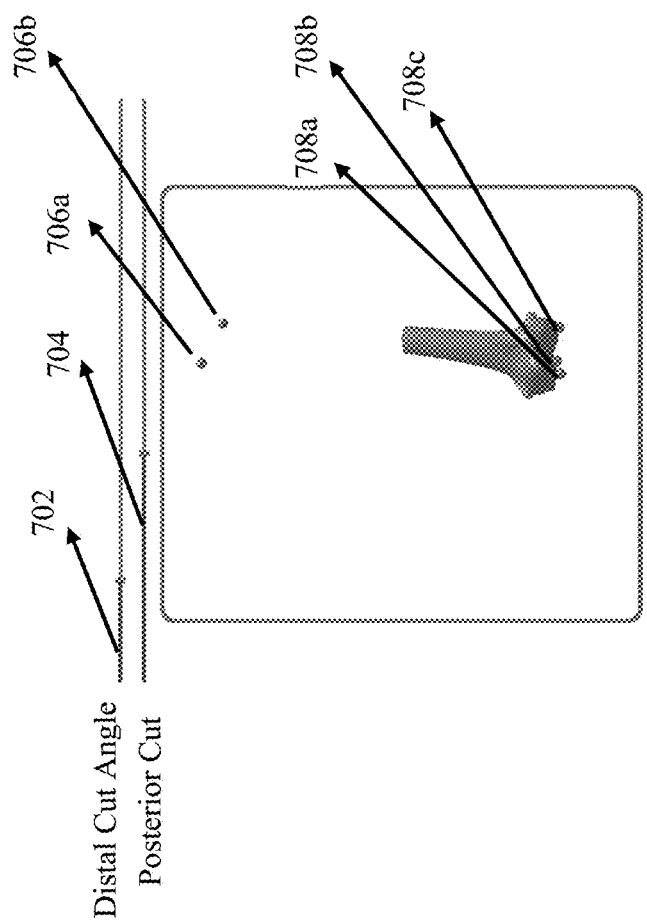
FIG. 7 illustrates an interface view during an auto landmarking, according to one or more embodiments.

FIG. 7 illustrates an interface view during the auto landmarking, according to one or more embodiments. The interface view (shown in FIG. 7) depicts one or more sliders 702, 704 of one or more parameters that are intended to adjust the kinematics on the region of interest. The one or more sliders 702, 704 allow the user to adjust the one or more parameters during the treatment (e.g. surgery). The parameters comprise at least one of but not limited to a depth of cut, a cut angle, the treatment location etc. The interface view further depicts the plurality of first points 706a, 706b of the first segment (e.g. hip) and the plurality of second points 708a, 708b, 708c of the second segment (e.g. knee). 706a is a hip center and 706b is a lesser trochanter location. The lesser trochanter 706b defines a posterior plane. The lesser trochanter 706b is where muscles attach to flex and extend. The user is enabled to adjust the kinematics associated with the plurality of first points 706a, 706b and the plurality of second points 708a, 708b, 708c by adjusting the one or more sliders on the interface view on the fly (i.e. during the treatment). In an embodiment, the system automatically adjusts the kinematics by automatically analyzing the region of interest and adjusting the one or more sliders based on the analysis for an optimum treatment. In another embodiment, the user is enabled to adjust the kinematics on the fly (i.e. during the treatment) that are automatically set by the system.

Figure 8:
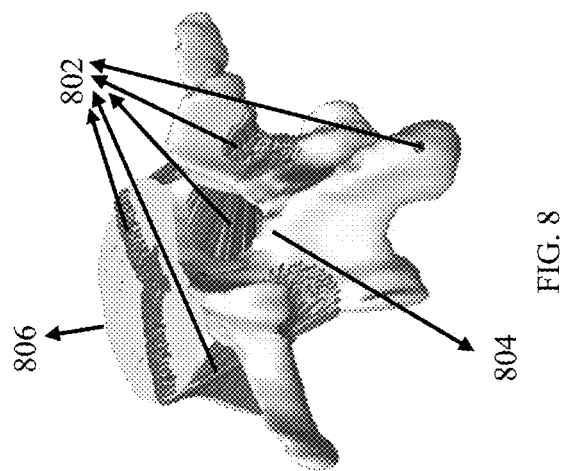
FIG. 8 illustrates a fourth processed image output of a virtual action depicting a treatment procedure on a region of interest, according to one or more embodiments.

FIG. 8 illustrates a fourth processed image output of the virtual action depicting the treatment procedure on the region of interest, according to one or more embodiments. The fourth processed image output shows a potential location 802 for the screw. The fourth processed image output may depict the trajectories for path of the screw. The fourth processed image output further shows the entry points of the screw and exit points of the screw. With respect to FIG. 8, the entry points are towards front side 804 of the region of interest (e.g. the hip) and the exit points are away from the front side (i.e. back side 806) of the region of interest (e.g. the hip). In an embodiment, the fourth processed image output shows the potential location of the screw. In an embodiment, the potential location of the screw is determined and indicated based on the density value associated with the region of interest (e.g. the hip), the length of the screw, the diameter of the screw and the pitch of the screw.

The fourth processed image output further indicates number of threads in the screw that are to be fixed in the region of interest.

For an instance, when the screw is of one millimeter, the fourth processed image output comprises a first number of the potential locations. When the screw is of eight millimeter, the fourth processed image output comprises a second number of the potential locations. The first number of the potential locations is higher than the second number of the potential locations, as the screw of one millimeter can fit most of the region of interest when compared to the screw of eight millimeter.

Figure 9A:
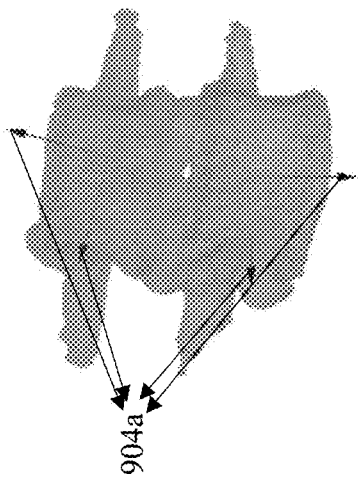
FIGS. 9a and 9b shows a region of interest in an unhealthy cluster state and a healthy cluster state respectively, according to one or more embodiments.
Figure 9B:
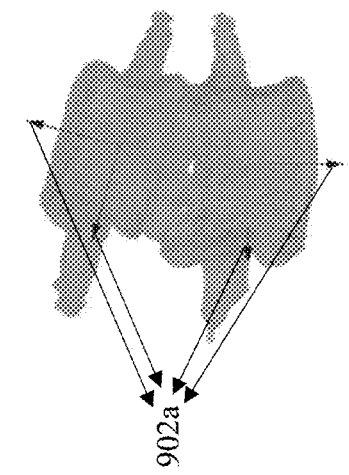

FIGS. 9a and 9b shows the region of interest in the unhealthy cluster state and the healthy cluster state respectively, according to one or more embodiments. The region of interest shown in FIGS. 9a and 9b is a first spinal bone in the unhealthy cluster state (e.g. a scoliosis state) and the healthy state, respectively. The first spinal bone is restored to the healthy cluster state from the scoliosis state based on the predefined virtual kinematic model associated with the healthy cluster state. FIGS. 9a and 9b dictates ligament and muscle lines acting on the first spinal bone to realign the unhealthy cluster state to the healthy cluster state. The ligament and muscle lines (e.g. tension) acting on the first spinal bone of the healthy cluster state is used to calculate and create the treatment plan (e.g. tension, muscle contraction, etc.) for the region of interest (i.e. the first spinal bone). The ligament and muscle lines acting on the first spinal bone of the healthy cluster state is used to track the trajectories for the screw. Further arrows 902a, 904a shown in FIGS. 9a and 9b depicts original co-ordinates of the first spinal bone prior to realigning the first spinal bone with a co-ordinates determination engine.

The co-ordinates determination engine comprises a physics engine that calculates an intervention location in polar co-ordinates rather than the original co-ordinates in order to perform the intervention and restore the first spinal bone to the healthy cluster state based on the predefined virtual kinematic model associated with the healthy cluster state. In the predefined virtual kinematic model, ligament and spinal spacing comprise optimization in six degrees of freedom. The ligament and muscle lines acting on the first spinal bone and the arrows 904a as indicated in FIG. 9b shows an optimum line length of the ligament and muscle lines, the polar co-ordinates and elasticity that is to be achieved so as to restore the first spinal bone from the scoliosis state to the healthy cluster state.

Figure 10:
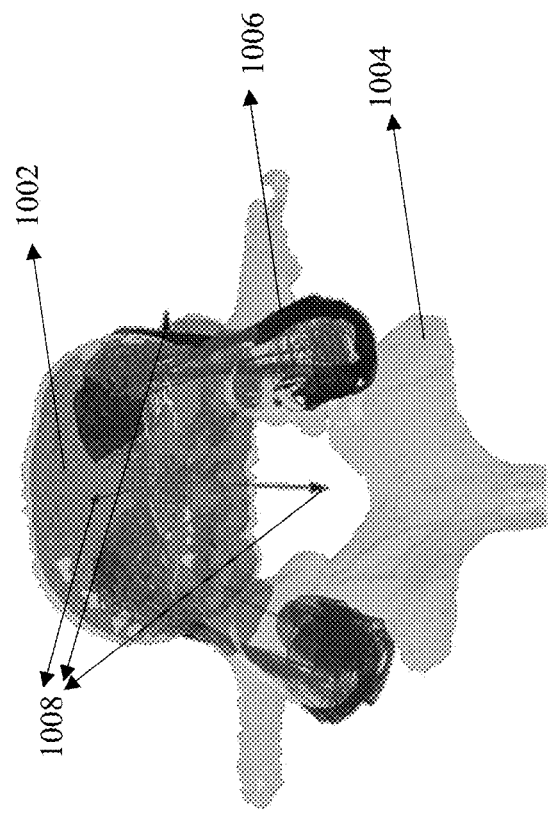
FIG. 10 illustrates an interface view of tracking a three-dimensional virtual kinematic model of a region of interest and depicting a treatment plan on the region of interest, according to one or more embodiments.

FIG. 10 illustrates an interface view of tracking the three-dimensional virtual kinematic model of the region of interest and depicting the treatment plan on the region of interest, according to one or more embodiments. The three-dimensional virtual kinematic model of the region of interest is generated and simulated based on the co-ordinates information and the density information extracted from the image file. The three-dimensional virtual kinematic model comprises the first segment 1002 (e.g. the first bone), the second segment 1004 (e.g. the second bone), and the third segment 1006 (e.g. the foreign object) indicated with the first color and the first identifier, the second color and the second identifier and the third color and the third identifier, respectively. The first segment 1002, the second segment 1004 and the third segment 1006 are readily distinguished to the user. The interface view depicts the ligament and muscle lines and arrows 1008 indicating the polar co-ordinates on the region of interest. The interface view further depicts at least one of a grouping of potential implant, the screw and plate position etc. on the region of interest. In an embodiment, the grouping implant, the screw, and the plate position are indicated with a fourth color, a fifth color, and a sixth color, respectively to readily identify and distinguish between the grouping implant, the screw, and the plate position.

Figure 11B:
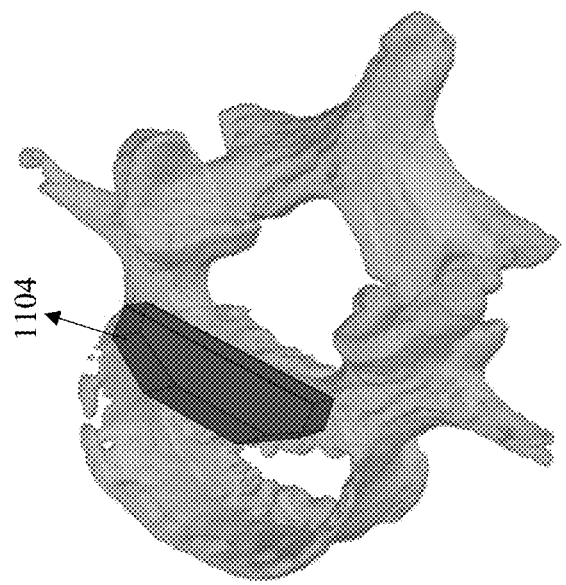
FIGS. 11a and 11b illustrates an interface view to a user that depicts an implant placement and adjusting/orienting the implant placement to an optimal location on a region of interest, according to one or more embodiments.
Figure 11A:
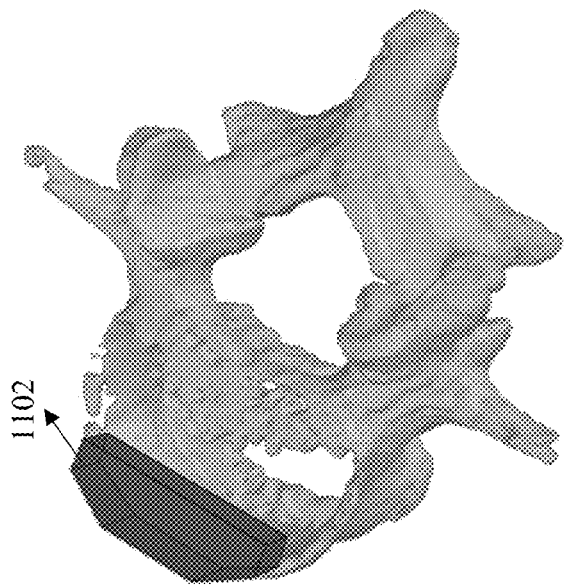

FIGS. 11a and 11b illustrates an interface view to the user that depicts an implant placement and adjusting/orienting the implant placement to an optimal location on the region of interest, according to one or more embodiments. The region of interest shown in FIGS. 11a and 11b is a second spinal bone. In an embodiment, the region of interest may be any part and/or any portion (e.g. the shoulder, the knee, the spine, etc.) of the living organism. The information extracting unit 210 of the server 202 extracts the co-ordinates information and the density information associated with the region of interest once the image file of the region of interest is received. The server 202 through the communication unit 228 communicates the processed image output to the device associated with the user.

The processed image output depicts the first segment (e.g. the dense bone), the second segment (e.g. the soft bone), the third segment (e.g. the foreign object), etc. based on the density information, the kinematics, the co-ordinates information and the point cloud information of the region of interest. The processed image output also depicts a first location, a second location, a third location, etc. on which the first segment, the second segment, the third segment are located and/or positioned, respectively. FIG. 11a depicts the implant placement at the first location 1102. The first location may be a random location selected/guessed by the user assuming that the first location is the location of the dense bone. The virtual kinematic model generation unit generates the virtual kinematic model of the region of interest (e.g. the second spinal bone) having the implant placement at the first location and simulates/runs the virtual kinematic model of the region of interest to determine whether the first location is the optimal location.

In an embodiment, the region of interest comprises a plurality of dense bones (e.g. a first dense bone, a second dense bone, a third dense bone, etc.). In another embodiment, the first segment (e.g. the dense bone) comprises the first dense bone, the second dense bone, the third dense bone, etc. The processed image output also depicts a fourth location, a fifth location, a sixth location, etc. on which first dense bone, the second dense bone, the third dense bone are located, respectively. The optimal location for the implant placement on the region of interest may vary from the first location, when the region of interest comprises the plurality of dense bones with different density values (i.e. when the region of interest comprises the first dense bone, the second dense bone, the third dense bone, etc.).

FIG. 11b depicts the implant placement adjusted/oriented to the optimal location 1104 based on at least one of the kinematics, the point cloud information, the density information and the co-ordinates information. The optimal location may comprise one of the fourth location, the fifth location, the sixth location, etc. The optimal location may comprise optimum attachment points. In an embodiment, the optimal location of the implant placement provides movement of six degree of freedom. The optimal location is determined and identified using a simulation. In an embodiment, the simulation comprises a Monte Carlo Simulation. In another embodiment, the optimal location is determined and identified by the server 202, considering the implant having maximum contact with the dense bone of the region of interest. The implant having the maximum contact with the dense bone of the region of interest provides optimum support and fixation. The optimal location comprises a location of densest bone possible among the region of interest.

In an embodiment, the interface view allows the user to select the optimal location (e.g. the fourth location, the fifth location, the sixth location, etc.) from the region of interest for the implant placement. In another embodiment, the interface view allows the user to select at least one of the first dense bone, the second dense bone, the third dense bone, etc. for the implant placement (i.e. the interface view allows the user to select the optimal location for the implant placement based on the density values). In yet another embodiment, the interface view allows the user to move the implant virtually in XYZ plane and rotate/orient the implant about its axis to have the maximum contact with the dense bone of the region of interest, cover maximum amount of joints on the region of interest and provide the optimum support. In yet another embodiment, the interface view allows the user to create a path (e.g. conical) for an implant that goes safe and fits into the optimal location of the region of interest without disturbing/hitting other portions on the region of interest. In yet another embodiment, the interface view enables the user to determine/make decision whether the implant needs to be rotated at any point within the region of interest to drag and place the implant at the optimal location of the region of interest. In yet another embodiment, the interface view allows the user to design the implant to fit at the optimal location of the region of interest based on the decision/determination.

In yet another embodiment, the interface view visually presents the implant placement at the optimal location, prevent subsidence and verify whether the implant placement covers actual area on the region of interest that are intended for the implant placement. In yet another embodiment, the user is allowed to bank the implant on the densest bone possible among the region of interest and not on any of the soft bone on the region of interest. In yet another embodiment, the interface view allows the user to determine and select trajectories of the implant. In yet another embodiment, the interface view allows the user to place a stent implant at the optimal location on the region of interest. In yet another embodiment, the interface view allows the user to change a size of the implant to fit to the region of interest. In yet another embodiment, the interface view allows the user to change the size of the implant with respect to the size of the dense bone on the region of interest. In yet another embodiment, the interface view allows the user to change the size of the implant with respect to the size available from a manufacturer of the implant.

In yet another embodiment, the interface view allows the user to change the size of the implant with respect to population (e.g. United States Population, Asian population, etc.) to which the region of interest belongs and with respect to aspect ratio. In yet another embodiment, the interface view allows the user to orient the implant on the region of interest to a first angle and determine whether the implant overhangs and/or under hangs on the region of interest and prevent the implant from protruding/hitting at least one of veins, arteries, bones, etc. on the region of interest. The interface view also depicts at least one treatment procedure indicating at least one of the size of the implant, the orientation, the optimal location etc. The interface view further enables the user to select the at least one treatment procedure that provides the implant placement with the optimum fixation at the region of interest. The optimal location may comprise a first optimal location, a second optimal location, etc. The interface view allows the user to perform the implant placement subsequently at the second optimal location, when the implant placement performed at the first optimal location fails to restore the kinematics in the region of interest. The optimal location for the optimum fixation on the region of interest is looped back/updated back on the database by the information recording unit. In yet another embodiment, the interface view allows the user to place an Anterior cruciate ligament (ACL), a medial collateral ligament (MCL) etc. at appropriate location in case of ACL, MCL tear etc. and the information recording unit updates/loops back the collective information on the database.

The foregoing disclosure provides illustration and description, but is not intended to be exhaustive or to limit the implementations to the precise form disclosed. Modifications and variations are possible in light of the above disclosure or may be acquired from practice of the implementations.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, etc. The invention may also be practiced in distributed system environments where local and remote computer systems, which are linked (either by hardwired data links, wireless data links, or by a combination of hardwired and wireless data links) through a network, both perform tasks. In a distributed system environment, program modules, units may be located in both local and remote memory storage devices.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

Although the present embodiments have been described with reference to specific example embodiments, it will be evident that various modifications and changes may be made to these embodiments without departing from the broader spirit and scope of the various embodiments. For example, the various devices, units and modules described herein may be enabled and operated using hardware circuitry (e.g., CMOS based logic circuitry), firmware, software or any combination of hardware, firmware, and software (e.g., embodied in a non-transitory machine-readable medium). For example, the various electrical structures and methods may be embodied using transistors, logic gates, and electrical circuits (e.g., application specific integrated (ASIC) circuitry and/or Digital Signal Processor (DSP) circuitry).

In addition, it will be appreciated that the various operations, processes, and methods disclosed herein may be embodied in a non-transitory machine-readable medium and/or a system. Accordingly, the specification and drawings are to be regarded in an illustrative rather than a restrictive sense.

INCORPORATION BY REFERENCE

All publications, patents, and patent applications cited in this Specification are hereby incorporated by reference in their entirety, including:

US20140093153A1 entitled "Method and System for Bone Segmentation and Landmark Detection for Joint Replacement Surgery";
US20190005186A1 entitled "Systems and methods for using generic anatomy models in surgical planning";
WO2020141812A1 entitled "Region of interest labeling device for bone marrow interpretation, and region of interest detection system comprising same";
EP2754419A2 entitled "Patient-adapted and improved orthopedic implants, designs and related tools";
EP1716535A2 entitled "Virtual endoscopy methods and systems";
US20150328004 entitled "Bone Reconstruction and Orthopedic Implants";
U.S. Pat. No. 9,452,050B2 entitled "Method incorporating computer-implemented steps, a computing device and a computer readable storage medium for developing manufacturing parameters for manufacturing an orthopaedic implant";
U.S. Ser. No. 10/292,770B2 entitled "Systems, methods, and devices for developing patient-specific spinal treatments, operations, and procedures";
U.S. Ser. No. 10/595,844B2 entitled "Systems and methods for surgical and interventional planning, support, post-operative follow-up, and functional recovery tracking";
US20080221923A1 entitled "Medical information management system";
WO2020037308A1 entitled "Patient-specific surgical method and system";
US20190183411A1 entitled "Virtual Ligament Balancing";
US20200205898A1 entitled "Systems and methods for surgical planning using soft tissue attachment points";
US20200170604A1 entitled "CT Based Probabilistic Cancerous Bone Region Detection";
U.S. Ser. No. 10/582,970B2 entitled "System and method for predicting tissue integrity".

What is claimed is:

1. A method comprising:
receiving an image file of a region of interest of an anatomy, wherein the anatomy comprises a bodily structure of a living organism;
extracting co-ordinates information and density information of a plurality of points of the image file;
pre-training a neural network based on the co-ordinates information, the density information and collective information available in a database, wherein the collective information comprises a plurality of clusters of different physiological states of the living organism;
performing at least one of a virtual action, and a treatment, via a user, on the region of interest based on an input from the neural network to generate an output for the user;
training the neural network based on at least one of a user input from the user, and the collective information from the database;
recording the co-ordinates information and the density information of the region of interest on the database;
recording first information, on the database, based on the virtual action and the treatment on the region of interest under a first cluster of the plurality of clusters of different physiological states to which the region of interest belongs; and
recording second information on the database, under the first cluster of the plurality of clusters of different physiological states to which the region of interest belongs, based on at least one of outcome of the treatment, and a feedback from the user.

2. The method of claim 1, wherein recording the second information on the database comprises updating the first information on the database based on at least one of the outcome of the treatment, and the feedback from the user.

3. The method of claim 1, wherein extracting the co-ordinates information and the density information of the plurality of points comprises:
creating point cloud information of the anatomy based on the co-ordinates information, the density information, and the collective information.

4. The method of claim 1, wherein performing at least one of the virtual action, and the treatment, via the user, on the region of interest comprises:
performing at least one of the virtual action, and the treatment on the region of interest through at least one of a virtual reality and an augmented reality.

5. A method comprising:
receiving an image file of a region of interest of an anatomy, wherein the anatomy comprises a bodily structure of a living organism;
extracting co-ordinates information and density information of a plurality of points of the image file;
pre-training a neural network based on the co-ordinates information, the density information and collective information available in a database, wherein the collective information comprises a plurality of clusters of different physiological states of the living organism;
performing at least one of a virtual action, and a treatment, via a user, on the region of interest based on an input from the neural network to generate an output for the user;
training the neural network based on at least one of a user input from the user, and the collective information from the database, wherein performing the virtual action comprises performing at least one of
segmenting a segment of the region of interest;
landmarking the segment of the region of interest;
labelling the segment of the region of interest; and
creating a treatment plan for the region of interest;
wherein segmenting the segment of the region of interest comprises:
generating a heat map based on point cloud information of the anatomy;
assigning a threshold value to the segment of the region of interest;
estimating Hounsfield units of the plurality of points of the image file;
outlining the segment of the region of interest; and
determining at least one of an edge and a tunnel on the region of interest based on the Hounsfield units.

6. The method of claim 5, wherein performing the virtual action further comprises:
recommending at least one of a treatment procedure, the treatment plan, and a treatment location of the region of interest based on the collective information in the database.

7. The method of claim 5, wherein determining at least one of the edge and the tunnel on the region of interest comprises:
determining density value of the plurality of points of the region of interest; and
determining a plurality of first points on the region of interest as at least one of the edge and the tunnel, when the plurality of first points comprises a first density value lower than a second density value of a plurality of second points, the plurality of second points located on either side of the plurality of first points.

8. The method of claim 5, wherein assigning the threshold value to the segment of the region of interest comprises:
   identifying a first segment and a second segment of the region of interest based on the co-ordinates information and the density information; and
   assigning a first threshold value and a second threshold value to the first segment and the second segment of the region of interest, respectively.

9. The method of claim 5, wherein landmarking the segment of the region of interest comprises:
   identifying a first cluster from the plurality of clusters of different physiological states to which the region of interest belongs;
   correlating a virtual kinematic model of the region of interest with a predefined virtual kinematic model of the first cluster;
   analyzing motion of the virtual kinematic model and predicting a constraint and a constraint location for the virtual kinematic model;
   determining a first position and a first angle for at least one of a ligament attachment point and a tendon attachment point in the virtual kinematic model at a first level; and
   determining a second position and a second angle for at least one of the ligament attachment point and the tendon attachment point in the virtual kinematic model at a second level, when the first position and first angle fails to create an optimum kinematics in the virtual kinematic model.

10. The method of claim 5, wherein creating the treatment plan for the region of interest comprises:
    analyzing a defect on the region of interest;
    simulating a virtual kinematic model of the region of interest;
    identifying a first cluster from the plurality of clusters of different physiological states to which the region of interest belongs;
    correlating the virtual kinematic model with a predefined virtual kinematic model of the first cluster;
    analyzing motion of the predefined virtual kinematic model and predicting a constraint and a constraint location for the virtual kinematic model; and
    creating at least one of a treatment procedure, the treatment plan, a tendon attachment point, and a ligament attachment point for the region of interest.

11. The method of claim 10, wherein identifying the first cluster from the plurality of clusters of different physiological states to which the region of interest belongs comprises:
    recording information associated with the region of interest under a new cluster when the region of interest does not belong to the first cluster, the new cluster comprises a sub-cluster.

12. The method of claim 10, wherein creating the treatment plan comprises:
    recovering kinematics and retaining an activity of daily living (ADL) of the living organism.

13. The method of claim 5, wherein performing the virtual action further comprises:
    generating at least one of a three-dimensional (3D) virtual kinematic model of the region of interest and a processed image file of the region of interest based on the co-ordinates information, the density information, and the collective information of the database;
    simulating the three-dimensional (3D) virtual kinematic model to virtually display functioning of the region of interest to the user; and
    assisting the user to perform the treatment on the region of interest.

14. The method of claim 13, wherein generating at least one of the three-dimensional (3D) virtual kinematic model of the region of interest and the processed image file of the region of interest comprises enabling at least one of an automated machine and a semi-automated machine to print a three-dimensional (3D) physical incarnation of at least one of the processed image file and the three-dimensional (3D) virtual kinematic model of the region of interest.

15. The method of claim 14, wherein printing the three-dimensional physical incarnation of at least one of the processed image file and the three-dimensional (3D) virtual kinematic model of the region of interest comprises indicating a first feature of the three-dimensional physical incarnation with a first color and a first identifier, and a second feature of the three-dimensional physical incarnation with a second color and a second identifier.

16. The method of claim 14, wherein the three-dimensional physical incarnation of at least one of the processed image file or the three-dimensional (3D) virtual kinematic model of the region of interest comprises a printed version of the anatomy with or without a tracking feature as part of the printed version configured to be tracked by a navigation tool to allow a visual representation of a bone location for a practice surgery on a plastic bone with cut and drill features clearly identified for practice.

17. The method of claim 16, further comprising tracking of the plastic bone, along with a conical or otherwise feature to limit a surgical tool to breach an area that should not be interfered.

18. The method of claim 17, wherein a robot or similar device mimics movements of the surgical tool relative to the plastic bone and repeats the movements of the surgical tool on the patient bone.

19. The method of claim 18, wherein the repeats of the movements of the surgical tool on the patient bone is performed either through wired communication or through a wireless communication protocol.

20. The method of claim 19, wherein the repeats of the movements of the surgical tool on the patient bone is performed either in a same room where the robot or similar device mimics movements of the surgical tool relative to the plastic bone or in a different room.

* * * * *

UNITED STATES PATENT AND TRADEMARK OFFICE
CERTIFICATE OF CORRECTION

PATENT NO. : 10,937,542 B1
APPLICATION NO. : 17/025458
DATED : March 2, 2021
INVENTOR(S) : Gokce Yildirim Page 1 of 1

It is certified that error appears in the above-identified patent and that said Letters Patent is hereby corrected as shown below:

In the Claims

Column 34, Line 6, replace "the" with --a--
Column 36, Line 46, replace "the" with --a--

Signed and Sealed this
First Day of June, 2021

Drew Hirshfeld
*Performing the Functions and Duties of the
Under Secretary of Commerce for Intellectual Property and
Director of the United States Patent and Trademark Office*